US010594715B2

United States Patent
(12) United States Patent
Fadlil et al.

(10) Patent No.: US 10,594,715 B2
(45) Date of Patent: Mar. 17, 2020

(54) APPARATUS FOR DETECTING ANOMALY AND OPERATING METHOD FOR THE SAME

(71) Applicant: SAMSUNG ELECTRONICS CO., LTD., Suwon-si (KR)

(72) Inventors: Junaidillah Fadlil, Jakarta (ID); Rudy Hario Pribadi, Jakarta (ID); Jung Sin Yi, Jakarta (ID); Sean H. Kim, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 186 days.

(21) Appl. No.: 15/854,953

(22) Filed: Dec. 27, 2017

(65) Prior Publication Data

US 2018/0183823 A1 Jun. 28, 2018

(30) Foreign Application Priority Data

Dec. 28, 2016 (ID) ............................ P00201609070
Dec. 13, 2017 (KR) ........................ 10-2017-0171420

(51) Int. Cl.

*H04L 29/06* (2006.01)
*G06Q 20/12* (2012.01)
*G06F 9/54* (2006.01)
*G16H 20/30* (2018.01)
*G06N 20/00* (2019.01)
*G06F 16/951* (2019.01)
(Continued)

(52) U.S. Cl.

CPC .......... *H04L 63/1425* (2013.01); *G06F 9/546* (2013.01); *G06F 11/00* (2013.01); *G06F 16/951* (2019.01); *G06N 20/00* (2019.01); *G06Q 20/12* (2013.01); *G16H 20/30* (2018.01); *G16H 40/20* (2018.01); *G16H 40/67* (2018.01); *G16H 50/20* (2018.01); *H04L 63/1416* (2013.01); *H04W 12/12* (2013.01); *G06Q 30/0226* (2013.01); *G06Q 30/0239* (2013.01)

(58) Field of Classification Search

CPC combination set(s) only.
See application file for complete search history.

(56) References Cited

U.S. PATENT DOCUMENTS 5,819,226 A 10/1998 Gopinathan et al.
8,745,641 B1 6/2014 Coker
(Continued)

OTHER PUBLICATIONS

Search Report dated Apr. 20, 2018, issued by the International Searching Authority in counterpart International Patent Application No. PCT/KR2017/015424 (PCT/ISA/210).
(Continued)

*Primary Examiner* — Malcolm Cribbs
(74) *Attorney, Agent, or Firm* — Sughrue Mion, PLLC

(57) ABSTRACT

Disclosed are an apparatus for detecting an anomaly and an operating method for the apparatus. The disclosed apparatus may include a communication interface, a memory including one or more instructions, and a processor configured to execute the one or more instructions to receive one or more application programming interface (API) calls corresponding to one or more applications from a terminal device, and determine whether the anomaly has occurred in a first pattern of data acquired from the received API calls, by using a second pattern of data stored in a database.

19 Claims, 25 Drawing Sheets

(51) Int. Cl.

| | |
|---|---|
| ***H04W 12/12*** | (2009.01) |
| ***G06F 11/00*** | (2006.01) |
| ***G16H 50/20*** | (2018.01) |
| ***G16H 40/20*** | (2018.01) |
| ***G16H 40/67*** | (2018.01) |
| *G06Q 30/02* | (2012.01) |

(56) References Cited

U.S. PATENT DOCUMENTS

| | | | | |
|---|---|---|---|---|
| 8,887,286 | B2 | 11/2014 | Dupont et al. | |
| 9,754,105 | B1 * | 9/2017 | Lopez-Chicheri | G06F 21/55 |
| 9,892,253 | B1 * | 2/2018 | Mehr | G06F 21/52 |
| 2007/0192863 | A1 * | 8/2007 | Kapoor | G06F 9/505 726/23 |
| 2007/0289013 | A1 | 12/2007 | Lim | |
| 2008/0222717 | A1 * | 9/2008 | Rothstein | H04L 63/1416 726/14 |
| 2009/0126017 | A1 * | 5/2009 | Chahal | G06F 21/54 726/23 |
| 2010/0180344 | A1 * | 7/2010 | Malyshev | G06F 21/566 726/23 |
| 2010/0228580 | A1 | 9/2010 | Zoldi et al. | |
| 2012/0222120 | A1 | 8/2012 | Rim et al. | |
| 2014/0130161 | A1 * | 5/2014 | Golovanov | G06F 21/564 726/23 |
| 2014/0207724 | A1 | 7/2014 | Ledenev et al. | |
| 2015/0127595 | A1 | 5/2015 | Hawkins, II et al. | |
| 2015/0135262 | A1 * | 5/2015 | Porat | G06F 21/552 726/1 |
| 2015/0161394 | A1 | 6/2015 | Ferragut et al. | |
| 2015/0180894 | A1 | 6/2015 | Sadovsky et al. | |
| 2015/0269050 | A1 | 9/2015 | Filimonov et al. | |
| 2016/0088006 | A1 | 3/2016 | Gupta et al. | |
| 2016/0103996 | A1 * | 4/2016 | Salajegheh | G06F 11/3024 726/25 |
| 2016/0182536 | A1 * | 6/2016 | Lindo | H04L 67/22 726/27 |
| 2016/0224798 | A1 | 8/2016 | Lim | |
| 2017/0270299 | A1 * | 9/2017 | Kim | G06F 21/566 |
| 2017/0366562 | A1 * | 12/2017 | Zhang | H04L 63/1416 |
| 2018/0007069 | A1 * | 1/2018 | Hunt | H04L 63/1416 |
| 2018/0082299 | A1 * | 3/2018 | Al Anbari | G06Q 20/4016 |

OTHER PUBLICATIONS

Written Opinion dated Apr. 20, 2018, issued by the International Searching Authority in counterpart International Patent Application No. PCT/KR2017/015424 (PCT/ISA/237).

* cited by examiner

Traffic report: The red line indicates an area with heavy traffic based on GPS information collected from vehicles present in the affected area.

FIG. 18
1810
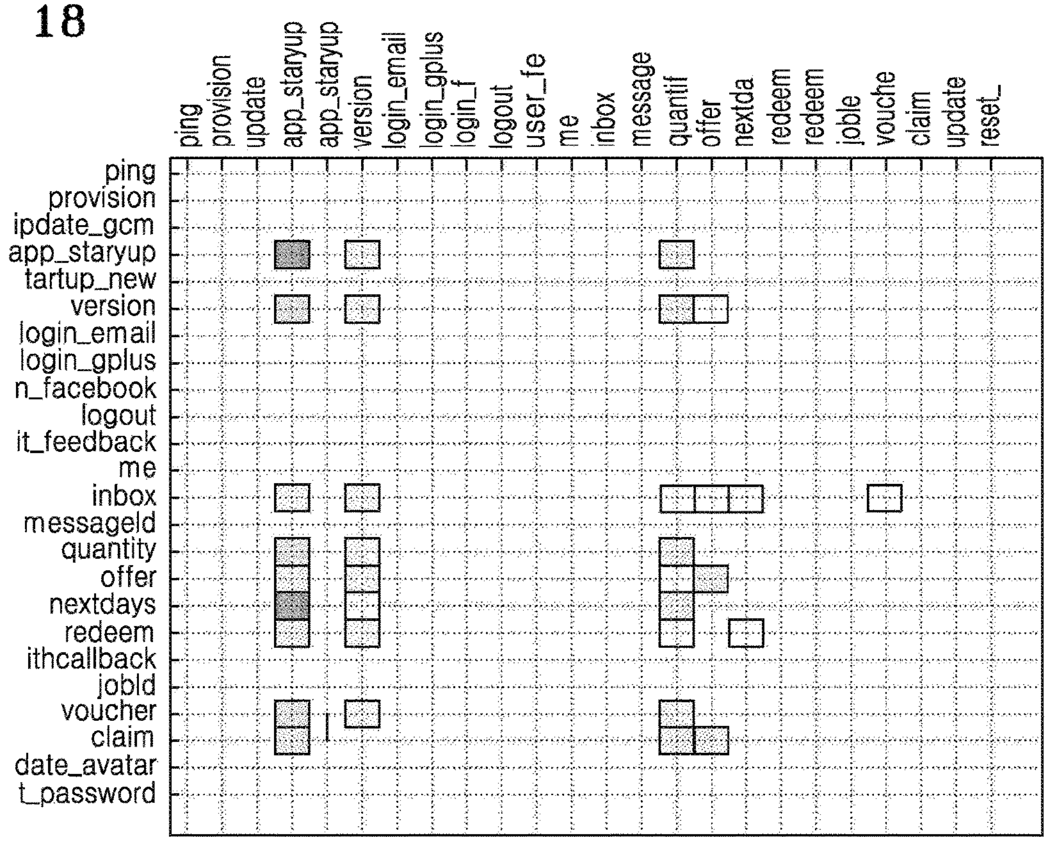
1820
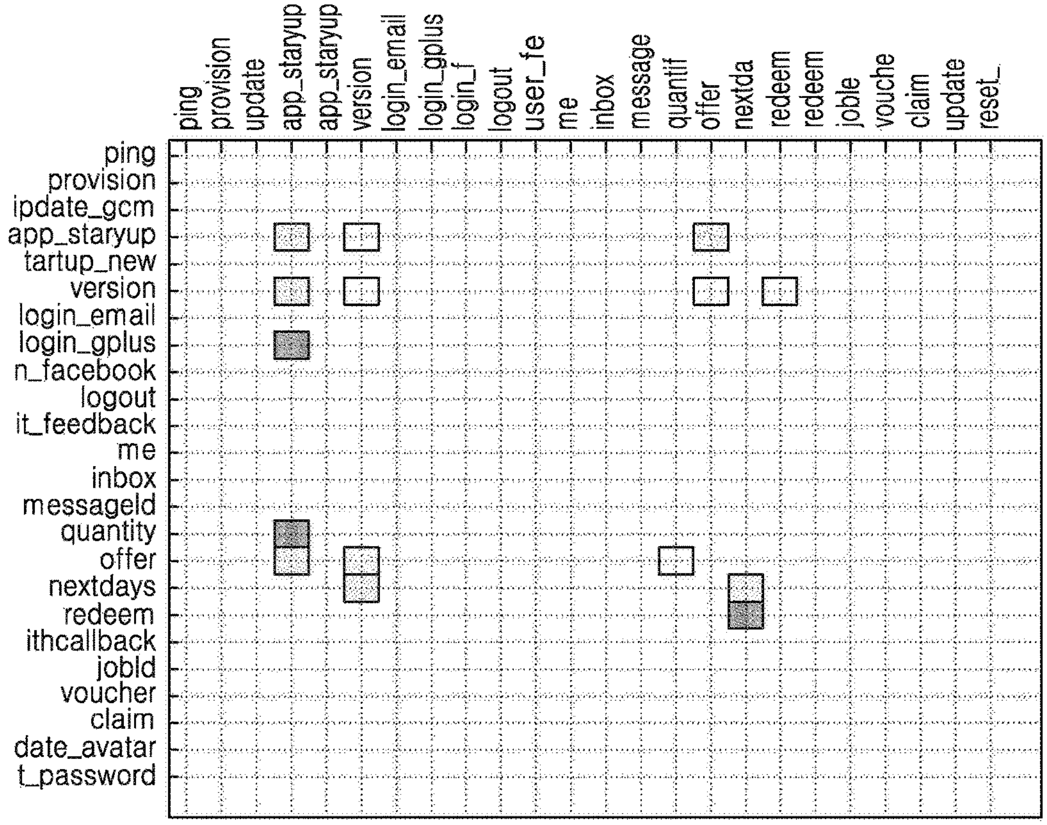

FIG. 20

```
" 120.188.0.85 - - [01/Dec/2016:10:48:45
+0000]                                  \"POST
/2.0/ggi/offer/claim.json?t-1480589326617&s=
f27be189-yyyy-xxxx-9272-
caa5d0938921&versionCode=1910000008
HTTP/1.1  \" 200  364 \"\"  \"\" 42580  372
\"https-frontend~\"\"priority\"\"serverx\" 2565
0 0 17 2582 -----441 433 22 4 0 0 0 \"\"\"\""
```

(a) API Call claiming coupon

```
" 112.215.171.70 - - [01/Dec/2016:10:55:38
+0000]                                  \"POST
/2.0/ggi/offer/redeem.json?t-1480589739054&
s=55b8bc-xxxx-yyyy-83de-
5d8e7045758&versionCode=1910000008
HTTP/1.1\" 202  743\"\"\"\"50374 924\"https-
frontend~\"\"priority\"\"serverx\" 95 0 1 14
110-----392 392 234 0 0 0 \"\"\"\""
```

(b) API Call for redeeming coupon

Anomaly Detection Report (2210)

| No | User | Probability |
|---|---|---|
| 1 | User 1 | $x^1$ |
| 2 | User 2 | $x^2$ |
| 3 | User 3 | $x^3$ |
| 4 | User 4 | $x^4$ |
| . | | |
| . | | |
| . | | |
| n | User n | $x^n$ |

Anomaly Detection Report (2220)

Details user 1

| Session (2221) | Duration (2222) | Number of Redeem (2223) |
|---|---|---|
| $s^1$ | $t^1$ | $r^1$ |
| $s^2$ | $t^2$ | $r^2$ |
| $s^3$ | $t^3$ | $r^3$ |
| . | | |
| $s^m$ | $t^m$ | $r^m$ |

Total session | Total Redeem

Block ? | Send to Training pool ?

APPARATUS FOR DETECTING ANOMALY AND OPERATING METHOD FOR THE SAME

CROSS-REFERENCE TO RELATED APPLICATIONS

This application claims priority from Indonesian Patent Application No. P-00201609070, filed on Dec. 28, 2016 in the Indonesia Patent Office, and Korean Patent Application No. 10-2017-0171420, filed on Dec. 13, 2017 in the Korean Intellectual Property Office, the disclosures of which are incorporated herein in their entirety by reference.

BACKGROUND

1. Field

The present disclosure relates to an apparatus for detecting an anomaly and an operating method for the apparatus, and more particularly, to an apparatus and method for detecting an anomaly in a web application and a sensing application.

2. Description of the Related Art

In recent years, many application programs use representational state transfer (REST) application programming interface (API) calls as backend communication of mobile applications, web applications, Internet of things (IoT) applications, and the like. Therefore, the need for building an anomaly detection system has become prominent. To achieve high accuracy, the anomaly detection system requires as much information as possible. Much information is necessary to gain insight into various aspects of a problem so that a model may differentiate a normal interaction from an abnormal interaction. In a web service application, there is much information to be collected from a user side such as user activity logs and device logs, from a backend side such as proxy logs and backend logs, and from a database side such as a transactional database and the overview of the transactional database. All the information from these components may be used to improve the performance of the anomaly detection system.

However, when massive information from all components of the user side, the backend side, the database side, and the like is used in the anomaly detection system as mentioned above, the amount of data to be processed becomes massive. Therefore, the system may be enlarged, and anomaly detection may consume much time.

SUMMARY

Provided are an apparatus and operating method for rapidly detecting an anomaly in a web application or a sensing application.

Additional aspects will be set forth in part in the description which follows and, in part, will be apparent from the description, or may be learned by practice of the presented example embodiments.

According to an aspect of an example embodiment, an apparatus for detecting an anomaly may include: a communication interface; a memory including one or more instructions; and a processor configured to execute the one or more instructions to receive one or more application programming interface (API) calls corresponding to one or more applications from a terminal device, and determine whether the anomaly has occurred in a first pattern of data acquired from the received API calls, by using a second pattern of data stored in a database.

The processor may be further configured to determine whether the first pattern of the data acquired from the received API calls deviates from the second pattern of the data stored in the database, and determine that the anomaly has occurred when it is determined that the first pattern of the data acquired from the received API calls deviates from the second pattern of the data stored in the database.

The processor may be further configured to perform preprocessing, extract a feature, perform learning through a learning model, and make a prediction to determine whether the anomaly has occurred.

The processor may be further configured to, when it is determined that the anomaly has occurred, transmit a notification indicating that the anomaly has occurred to the terminal device.

The processor may be further configured to receive the one or more API calls generated by a transactional application from the terminal device, and determine whether the anomaly has occurred, by using the first pattern of the data acquired from the received API calls and a transactional data pattern stored in the database.

The transactional application may be at least one of an e-commerce application, a bank transaction application, and a coupon reward application.

The processor may be further configured to receive the one or more API calls generated by a sensing application from the terminal device, and determine whether the anomaly has occurred, by using the first pattern of the data acquired from the received API calls and a sensing data pattern stored in the database.

The sensing application may be at least one of an Internet of things (IoT) application, a healthcare application, and a location information detection application.

When the one or more applications are transactional applications, the data acquired from the API calls may be the API calls themselves, and when the one or more applications are sensing applications, the data acquired from the API calls may be signal data transferred through the API calls.

According to an aspect of an example embodiment, an operating method of an apparatus for detecting an anomaly may include: receiving one or more API calls corresponding to one or more applications from a terminal device; determining whether the anomaly has occurred in a first pattern of the data acquired from the received API calls, by using a second pattern of data stored in a database; and transmitting a notification indicating that the anomaly has occurred to the terminal device according to whether the anomaly has occurred.

According to an aspect of an example embodiment, provided is a non-transitory computer-readable recording medium having recorded thereon a program, which, when executed by a computer, performs the operating method.

BRIEF DESCRIPTION OF THE DRAWINGS

These and/or other aspects will become apparent and more readily appreciated from the following description of the example embodiments, taken in conjunction with the accompanying drawings in which:

FIG. 18 shows samples of a relative entropy matrix as a feature;

FIG. 20 shows an example of application programming interface (API) calls for using and claiming a coupon in a loyalty program;

DETAILED DESCRIPTION

Figure 1:
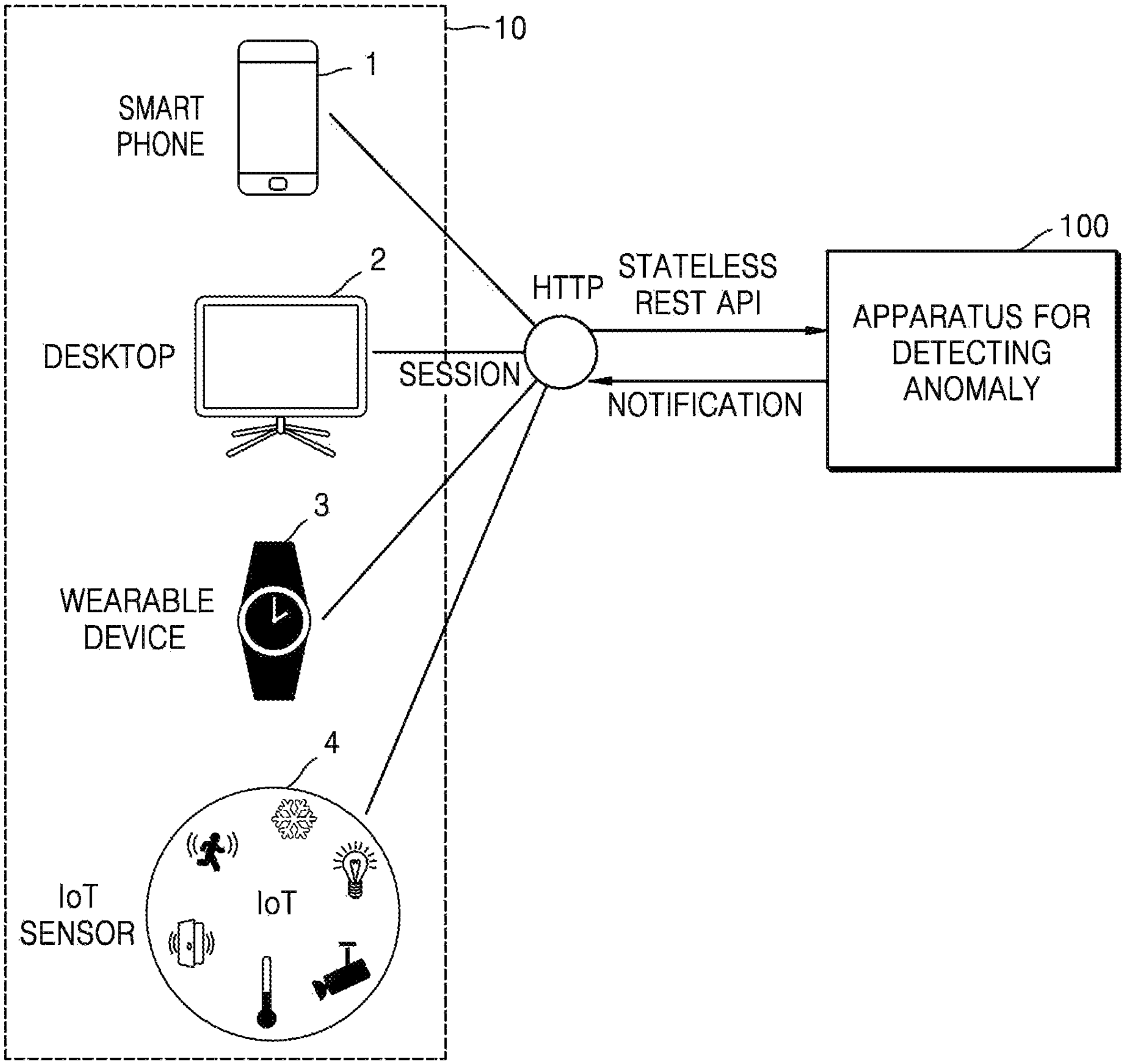
FIG. 1 shows an overview of a system for detecting an anomaly according to an example embodiment.

Terminology used in this specification will be briefly described, and then the present disclosure will be described in detail.

As terminology used in this specification, general terms currently in wide use are selected wherever possible in consideration of functions in the present disclosure, but may vary according to intentions of those of ordinary skill in the art, precedent cases, the advent of new technology, and the like. In particular, some terms may be specifically defined by the applicant, and in such cases, the detailed meanings of the terms will be stated in the corresponding description. Therefore, the terms used in this specification should be defined based on the meanings of the terms together with the description throughout the present disclosure rather than simple names thereof.

Throughout the specification, when a part is described as "including" an element, unless otherwise described, another element may also be included, rather than the presence of other elements being excluded. Also, terms such as "-er (-or)," "module," and the like used herein indicate a unit for processing at least one function or operation, in which the unit may be embodied as hardware (e.g., circuits, microchips, processors, etc.), software or a combination of hardware and software.

Reference will now be made in detail to example embodiments, which are illustrated in the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures, to explain aspects. In the drawings, content irrelevant to the description will be omitted to clearly describe the present disclosure. Expressions such as "at least one of," when preceding a list of elements, modify the entire list of elements and do not modify the individual elements of the list.

An anomaly refers to any behavior, event, condition, or phenomenon that deviates from what is defined, predefined or prescribed as an acceptable range of values, parameters or measurements by a user, an administrator, a service provider or the like.

In example embodiments of this specification, the term "user" denotes a person who controls functionality or operation of an image display device using a control device and may include a viewer, an administrator, or an installation engineer.

An apparatus for detecting an anomaly according to various example embodiments may detect an anomaly using only an application programming interface (API) call logs (proxy logs) and an overview of a transactional database. As digital transactions grow both in volume and speed, the necessity of real-time processing and warning have become one of the key parts of basic services that all companies have to provide to their customers. Nevertheless, due to increased security data encoding and growing data size, not all the information is visible at a representational state transfer (REST) API call level. Therefore, most companies require a new method for filtering out anomalies with insufficient information available at the REST API level to reduce anomaly candidates for additional processing.

Most related arts focus on financial transactions and user profiles. Existing anomaly detection methods focus on detecting anomalies by analyzing all complete information from various sources and applying rule-based or classical machine learning techniques, whereas the present disclosure automatically provides insights and detects a potential anomalous event from REST API calls from connected applications (apps)/sensors with limited information.

The present disclosure proposes a new scheme of detecting an anomalous event as digital transactions grow both in volume and speed, real-time processing is increased in speed and advanced, and all companies nowadays are using REST APIs to transmit all necessary information. The present disclosure proposes a method and system for detecting an anomalous event from REST API calls from connected apps/sensors, and the method and system may process streaming unstructured data and user/system behavior shifts. Furthermore, the system may learn data and obtain insights using API call logs.

In the system of the present disclosure, a small part of information is used, which makes the system fast and suitable for an early warning system. The present disclosure is an advisory system for anomalous events because of using a small part of information resulting in lower detection accuracy compared to using all the information. When a human-in-loop anomaly monitoring system is added to the present disclosure, since a system administrator is warned upon the occurrence of an anomalous activity, it is possible to reduce the number of anomalous activities that require additional processing.

An anomaly detection and response system of the present disclosure brings several advantages. First, a system for detecting an anomaly according to example embodiments has a high response rate. In emergency, the system for detecting an anomaly may be very useful for, for example, a user with an abnormal heart condition or another serious condition that requires immediate treatment.

The system for detecting an anomaly according to example embodiments promotes fairness. For example, the system prevents a user from performing an abnormal activity. As an example, the system may block an abnormal user who takes a lot of coupons in e-commerce so that others may not acquire the coupons.

The system for detecting an anomaly according to example embodiments has a self-control ability. For example, a driver may know whether his or her driving behavior is safe through anomaly detection.

The system for detecting an anomaly according to example embodiments may acquire information. It is possible to obtain many kinds of information from the system for detecting an anomaly. For example, a driver may obtain information on roadblocks or information on traffic jam of a particular road section.

Due to its simplicity, the system according to example embodiments may be applied in many fields, such as bank transaction, e-commerce, and loyalty collection platform in transactional applications as well as smart home, smart car, and smart things in mobile sensing applications without the need to explicitly define rules or characteristics of anomalies. A requirement for an explicit definition of an anomaly can be counterproductive and time-consuming. By applying a representation learning and online sequence labeling method to anomaly filtering based on API calls, the system may provide insight and detect an anomalous event from any similar preferences for REST API calls for both transactional and mobile sensing data processing.

The present disclosure develops a method and system for detecting an anomalous event from REST API calls in connected apps/sensors, which may process streaming unstructured data and user/system behavior shifts by the following operations including:

Building an integrated development environment and a streaming query-complex processing workflow model, where a user or an administrator may build and customize the system through a workflow designer by processing input data, preprocessing data, formatting data, extracting information, generating a predictive model, and implementing the model for detecting anomalous events, which may be performed through a computer or a mobile device;

Providing a data browser system that enables a user or an administrator to see details of data including new incoming streaming; and Automatically executing real-time anomaly detection for determining an anomalous state in a REST API call system through a complex event processing engine that performs data processing based on characteristics of input data; and applying the representation learning and online sequence labeling method to filter out anomalies based on API calls.

Next, the present disclosure continuously improves the accuracy of its anomaly prediction and reduces the number of anomalies that require additional processing by the following operations including: building a human-in-loop anomaly monitoring system that warns a user or an administrator in real time when an anomalous event or a behavior shift is detected; and incorporating a response system so that the system may transmit a notification to a device connected to a user.

FIG. 1 shows an overview of a system for detecting an anomaly according to an example embodiment.

In general, a system for detecting an anomaly requires many data resources to accurately determine whether a particular event is anomalous. Data resources may be obtained from device logs, user activity logs (captured from devices), proxy logs, backend logs, a transactional application database, and the like. However, the system for detecting an anomaly according to example embodiments may detect an anomaly in an application using a web service and an overview of a transactional database.

Referring to FIG. 1, terminal devices 10 may transmit information, for example, a session identifier (ID), a time query, and the like, to a server using a stateless REST API call. The terminal devices 10 may include any device that includes a processor and a transceiver and is capable of communication. In FIG. 1, the terminal devices 10 include a smart phone 1, a desktop computer 2, a wearable device 3, and Internet of things (IoT) sensors 4. However, the terminal devices 10 are not limited thereto and may be implemented as various electronic devices such as a tablet personal computer (PC), a digital camera, a camcorder, a laptop computer, an e-book terminal, a digital broadcast terminal, a personal digital assistant (PDA), a portable multimedia player (PMP), a navigation device, an digital audio player, a wearable device, and the like.

An apparatus 100 for detecting an anomaly may receive API calls generated by one or more applications executed in the terminal devices 10 and detect an anomalous pattern by processing the received API calls through a mechanism. Also, when an anomalous pattern is detected, the apparatus 100 for detecting an anomaly may provide a notification to a user. The notification may be determined variously according to application and device.

Applications executed in the apparatus 100 for detecting an anomaly may include a transactional application and a sensing application.

The apparatus 100 for detecting an anomaly may receive all information as time-series data. Also, the apparatus 100 for detecting an anomaly may manage and process the information as discrete or continuous time-series data according to device type.

A session is a concept for maintaining a state between a client and a server. When a client makes an initial connection, a unique session ID is given to the client. The client may automatically and temporarily store the session ID in a cookie, or may append the session ID to the end of a uniform resource locator (URL) when no cookie is supported. Such a session ID may be a means for identifying the corresponding client when the client makes a connection again. The session ID may be a string of an arbitrary length. The server needs to have the same session ID, and may identify the client when the client makes a request to the server with the given session ID.

Figure 2:
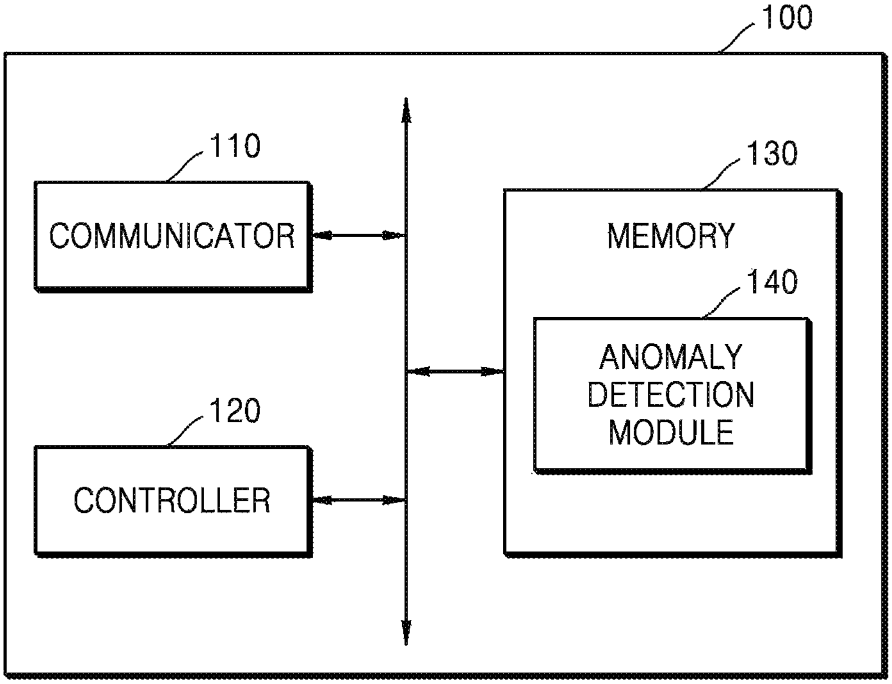
FIG. 2 is a block diagram of an apparatus for detecting an anomaly according to an example embodiment.

FIG. 2 is a block diagram of an apparatus for detecting an anomaly according to an example embodiment.

Referring to FIG. 2, the apparatus 100 for detecting an anomaly includes a communicator 110, a controller 120, and a memory 130.

The communicator 110 may connect the apparatus 100 for detecting an anomaly to an external terminal device 10 under control of the controller 120. The communicator 110 may include one of a wireless local area network (WLAN) module and an Ethernet module. Also, the communicator 110 may include a combination of a WLAN module and an Ethernet module.

The memory 130 may store various data, programs, or applications for operating and controlling the apparatus 100 for detecting an anomaly under control of the controller 120.

The memory 130 may store an operating system (OS) for controlling the apparatus 100 for detecting an anomaly and the controller 120, applications initially provided by a manufacturer or downloaded from the outside, a graphical user interface (GUI) related to the application, objects for providing the GUI (e.g., image text, icons, buttons, etc.), documents, databases, and related data.

The memory 130 includes a read-only memory (ROM), a random access memory (RAM), or a memory card (e.g., a micro secure digital (SD) card or a universal serial bus (USB) memory) installed in the apparatus 100 for detecting an anomaly. Also, the memory 130 may include a non-volatile memory, a volatile memory, a hard disk drive (HDD), or a solid-state drive (SSD).

In particular, the memory 130 may include an anomaly detection module 140 according to an example embodiment. The anomaly detection module 140 may include one or more instructions for receiving API calls generated by one or more applications and detecting an anomaly from the received API calls.

The controller 120 functions to control overall operation of the apparatus 100 for detecting an anomaly and signal flows between components in the apparatus 100 for detecting an anomaly and to process data. When there is an input of a user or a preset and stored condition is satisfied, the controller 120 may execute the operating system (OS) and various applications stored in the memory 130 and one or more applications stored in the anomaly detection module 140.

The controller 120 may include a RAM that stores a signal or data input from the outside of the apparatus 100 for detecting an anomaly or is used as a storage area corresponding to various tasks performed by the apparatus 100 for detecting an anomaly, a ROM in which a control program for controlling the apparatus 100 for detecting an anomaly is stored, and a processor.

The processor used in the controller 120 may be implemented as a system on chip (SoC) in which a core and a graphics processing unit (GPU) are integrated. Also, the processor may include a plurality of processors and/or cores. For example, the processor may be implemented as a main processor and a sub-processor that operates in a sleep mode.

By executing the one or more instructions stored in the memory 130, the controller 120 according to an example embodiment may receive one or more API calls corresponding to one or more applications and determine whether an anomaly has occurred in a pattern of data acquired from the received API calls using a data pattern stored in a database.

By executing the one or more instructions stored in the memory 130, the controller 120 according to an example embodiment may determine whether the pattern of the data acquired from the received API calls deviates from the data pattern stored in the database, and determine that an anomaly has occurred when it is determined that the pattern of the data acquired from the received API calls deviates from the data pattern stored in the database.

By executing the one or more instructions stored in the memory 130, the controller 120 according to an example embodiment may perform preprocessing, extract a feature, perform learning through a learning model, and make a prediction to determine whether an anomaly has occurred.

By executing the one or more instructions stored in the memory 130, the controller 120 according to an example embodiment may transmit a notification indicating that an anomaly has occurred to the terminal device when it is determined that an anomaly has occurred.

By executing the one or more instructions stored in the memory 130, the controller 120 according to an example embodiment may receive one or more API calls generated by the transactional application from the terminal device, and determine whether an anomaly has occurred using a pattern of data acquired from the received API calls and a transactional data pattern stored in a database.

According to an example embodiment, the transactional application may include at least one of an e-commerce application, a bank transaction application, and a coupon reward application.

By executing the one or more instructions stored in the memory 130, the controller 120 according to an example embodiment may receive one or more API calls generated by the sensing application from the terminal device and determine whether an anomaly has occurred using a pattern of data acquired from the received API calls and a sensing data pattern stored in a database.

According to an example embodiment, the sensing application may include at least one of an IoT application, a healthcare application, and a location information detection application.

According to an example embodiment, when the one or more applications are transactional applications, the data acquired from the API calls may be the API calls themselves, and when the one or more applications are sensing applications, the data acquired from the API calls may be signal data transferred through the API calls.

Meanwhile, the block diagram of the apparatus 100 for detecting an anomaly shown in the drawing is intended for an example embodiment. Each component of the block diagram may be integrated, added, or omitted according to specifications of the actually implemented apparatus 100 for detecting an anomaly. In other words, two or more components may be combined into one component, or one component may be subdivided into two or more components. Also, a function performed by each block is to describe example embodiments, and a detailed operation or device thereof does not limit the scope of the present disclosure.

Figure 3:
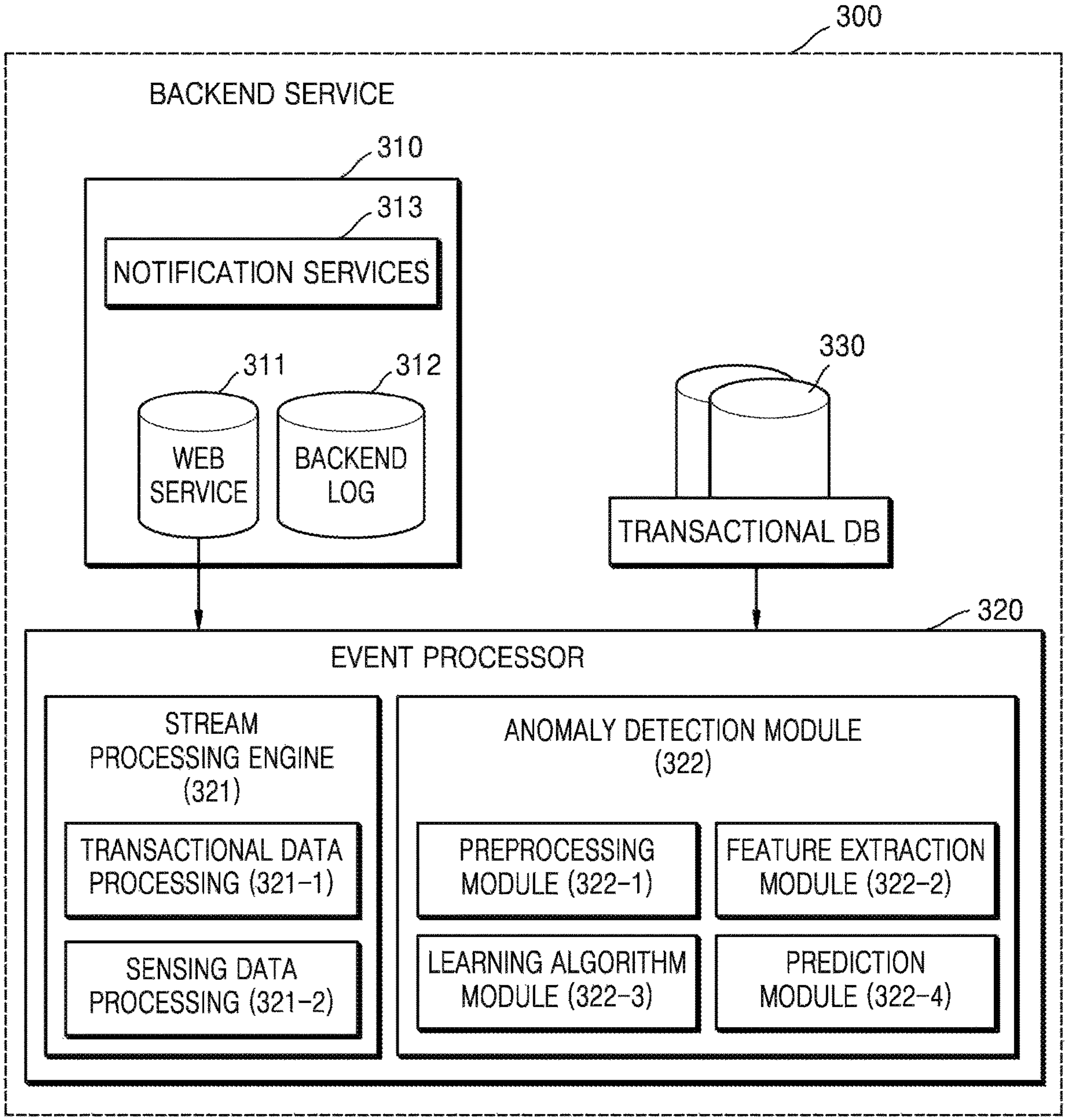
FIG. 3 shows an example of an apparatus for detecting an anomaly in terms of data according to an example embodiment.

FIG. 3 shows an example of an apparatus for detecting an anomaly in terms of data according to an example embodiment. Various modules and components shown in FIG. 3 and other figures may be implemented with hardware, software or a combination of both.

Referring to FIG. 3, an apparatus 300 for detecting an anomaly includes a backend service 310, an event processor 320, and a transactional database 330.

The backend service 310 includes a web service 311 for providing various services to a terminal device through the Web, a backend log 312, and a notification service 313 for providing a notification service to the terminal device when an anomaly is detected by the event processor 320.

The event processor 320 includes a stream processing engine 321 and an anomaly detection module 322.

The stream processing engine 321 may process input data based on characteristics of the data. Input data of transactional data processing 321-1 is an API call function, and input data of sensing data processing 321-2 may be an API call function or a real-time signal.

The anomaly detection module 322 may detect an anomaly based on the input data processed by the stream processing engine 321 and the transactional database 330.

The anomaly detection module 322 may include a preprocessing module 322-1, a feature extraction module 322-2, a learning algorithm module 322-3, and a prediction module 322-4.

The preprocessing module 322-1 is a function used to arrange the input data and convert data into a necessary format. When information of new incoming data is given, a next process searches the data with a specific session and obtains historical information.

The feature extraction module 322-2 extracts a feature from the preprocessed data.

A first operation of a feature extraction process involves generating a feature based on relative entropy. In this operation, a relationship between API calls is calculated. Next, a feature is generated based on a statistical time period of API calls, which may be processed independently in parallel to speed up the process. In the end, two features are combined to make a complete feature for a next process. In this system, relative entropy information between an API call and statistical time period information of the API call is used.

The learning algorithm module 322-3 is used in a learning algorithm model.

The prediction module 322-4 predicts whether the new incoming data is suspicious based on the given historical information of the session.

The transactional database 330 may store a history of data corresponding to an API call received from the terminal device.

Figure 4:
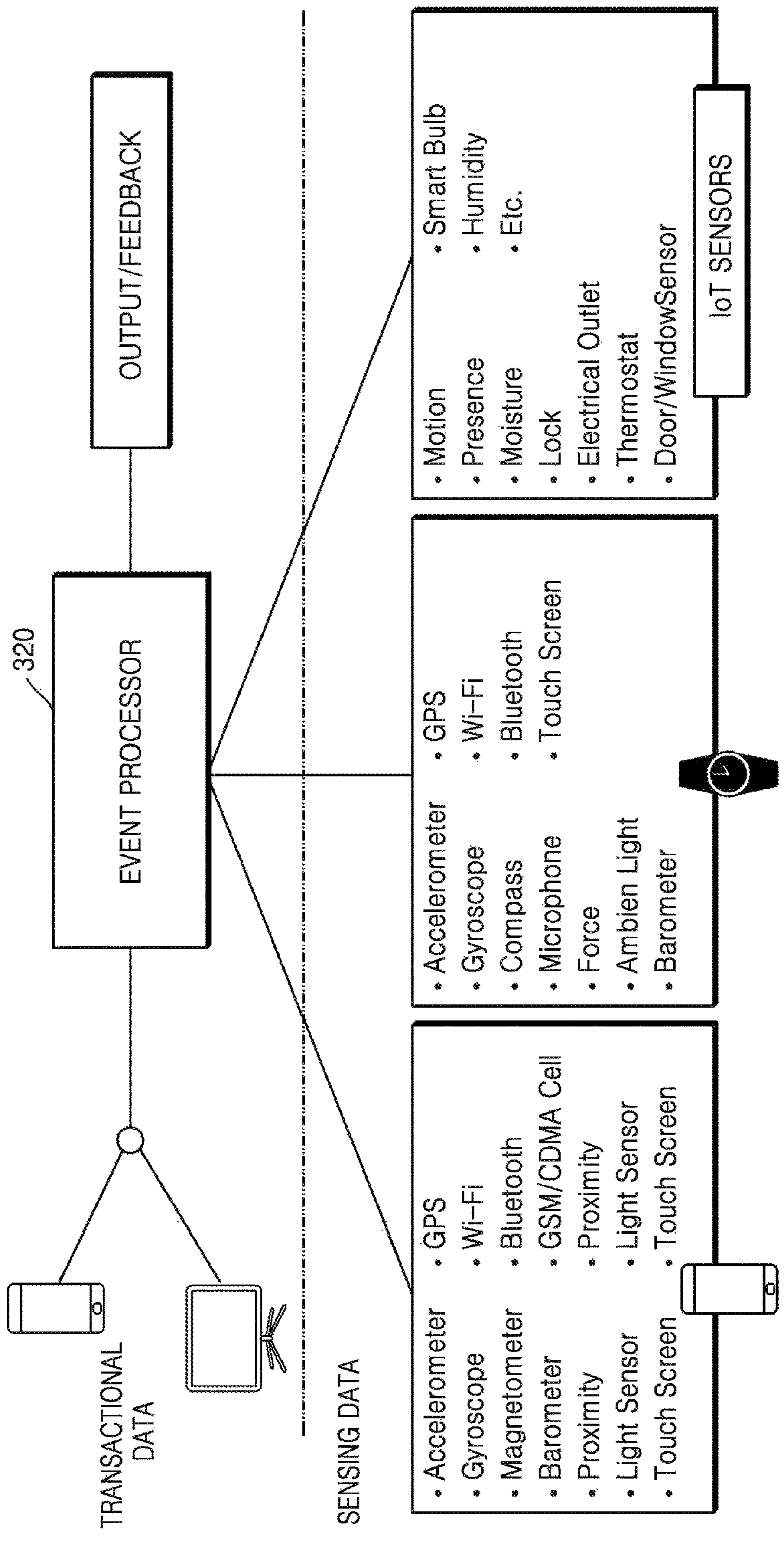
FIG. 4 shows an overview of applications used in an example embodiment.

FIG. 4 shows an overview of applications used in an example embodiment.

One or more applications used in an example embodiment may include a transactional application and a sensing application.

Referring to FIG. 4, two types of applications are used in an event processor system. The first type of application is a transactional application. For example, transactional applications include bank transaction applications, e-commerce applications, loyalty platform applications, and the like. This type of application calls a REST API mostly from user activities for the application. Here, it is possible to see the intention of a user by observing the REST API call.

The second type of application is a mobile sensing application that uses many sensors provided by a mobile device to interact with a user (e.g., motion tracking, automotive driving behavior detection, human activity control, or mobile sensing for healthcare by a running application). A sensor triggered by a user activity in the second type of application calls a REST API. Here, different sensors may be used depending on the needs of an application program.

For each type of application, the system attempts to detect an anomalous event. Input data for these two types of applications are also different. In transactional applications, the number of REST API calls may vary. Therefore, information of an API is the API itself.

In transactional applications, API calls may be various forms of calls. For example, in a mobile app, an open app API call, a close app API call, a redeem coupon API call, and the like may exist as access API calls. Here, API calls themselves represent different actions that an application user tries to perform. Therefore, API calls themselves represent activity information of a user.

On the other hand, sensing applications are usually used for a limited purpose. Therefore, an output of data is continuous time-series information.

However, in sensing applications, what is obtained through some API calls is data. For example, data obtained from a heart monitoring app is time-series heartbeat data. Therefore, API calls are not parts of information, but data transferred through the API calls is information. Since data of the two types of applications differ from each other, example embodiments may include two modes, that is, a transactional data processing mode and a mobile sensing data processing mode.

In the transactional data mode, a user who does not request a general API call may be an "anomaly" in bank transaction data according to a frequency or a sequence, and an abnormal signal may be an "anomaly" in time-series mobile sensing data. For example, the time-series mobile sensing data is a frequency or an amplitude of heartbeats.

Figure 5:
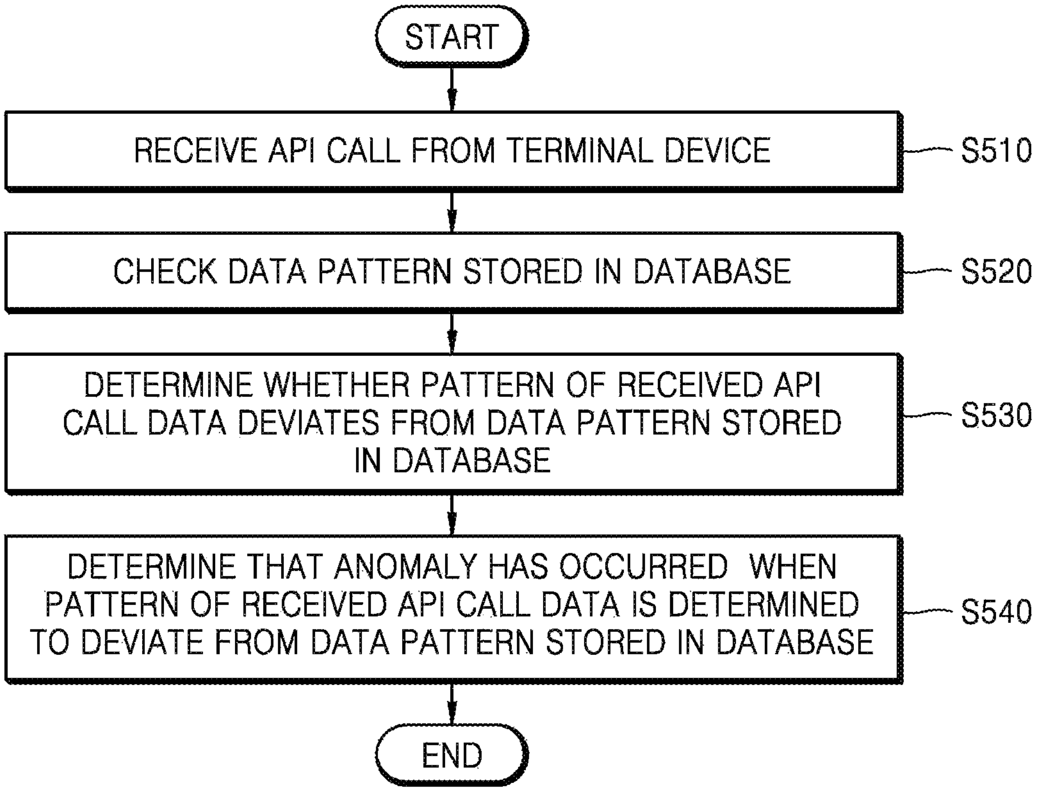
FIG. 5 is a flowchart illustrating operation of an apparatus for detecting an anomaly according to an example embodiment.

FIG. 5 is a flowchart illustrating operation of an apparatus for detecting an anomaly according to an example embodiment.

Referring to FIG. 5, in operation S510, the apparatus for detecting an anomaly may receive an API call from a terminal device.

According to an example embodiment, the apparatus for detecting an anomaly may receive one or more API calls generated by a transactional application executed by the terminal device.

According to an example embodiment, the apparatus for detecting an anomaly may receive one or more API calls generated by a sensing application executed by the terminal device (S510). The one or more API calls generated by the sensing application may transfer sensed signal data.

In operation S520, the apparatus for detecting an anomaly may check a data pattern stored in a database.

The apparatus for detecting an anomaly may check historical data of API call data stored in the database.

In operation S530, the apparatus for detecting an anomaly may determine whether a data pattern of the received API call deviates from the data pattern stored in the database.

The apparatus for detecting an anomaly may determine whether the data pattern of the received API call deviates from a pattern of the historical data stored in the database.

In operation S540, when it is determined that the data pattern of the received API call deviates from the data pattern stored in the database, the apparatus for detecting an anomaly may determine that an anomaly has occurred.

When it is determined that an anomaly has occurred, the apparatus for detecting an anomaly may transmit a notification indicating that an anomaly has occurred to the terminal device that has transmitted the API call or another device related to the terminal device.

Figure 6:
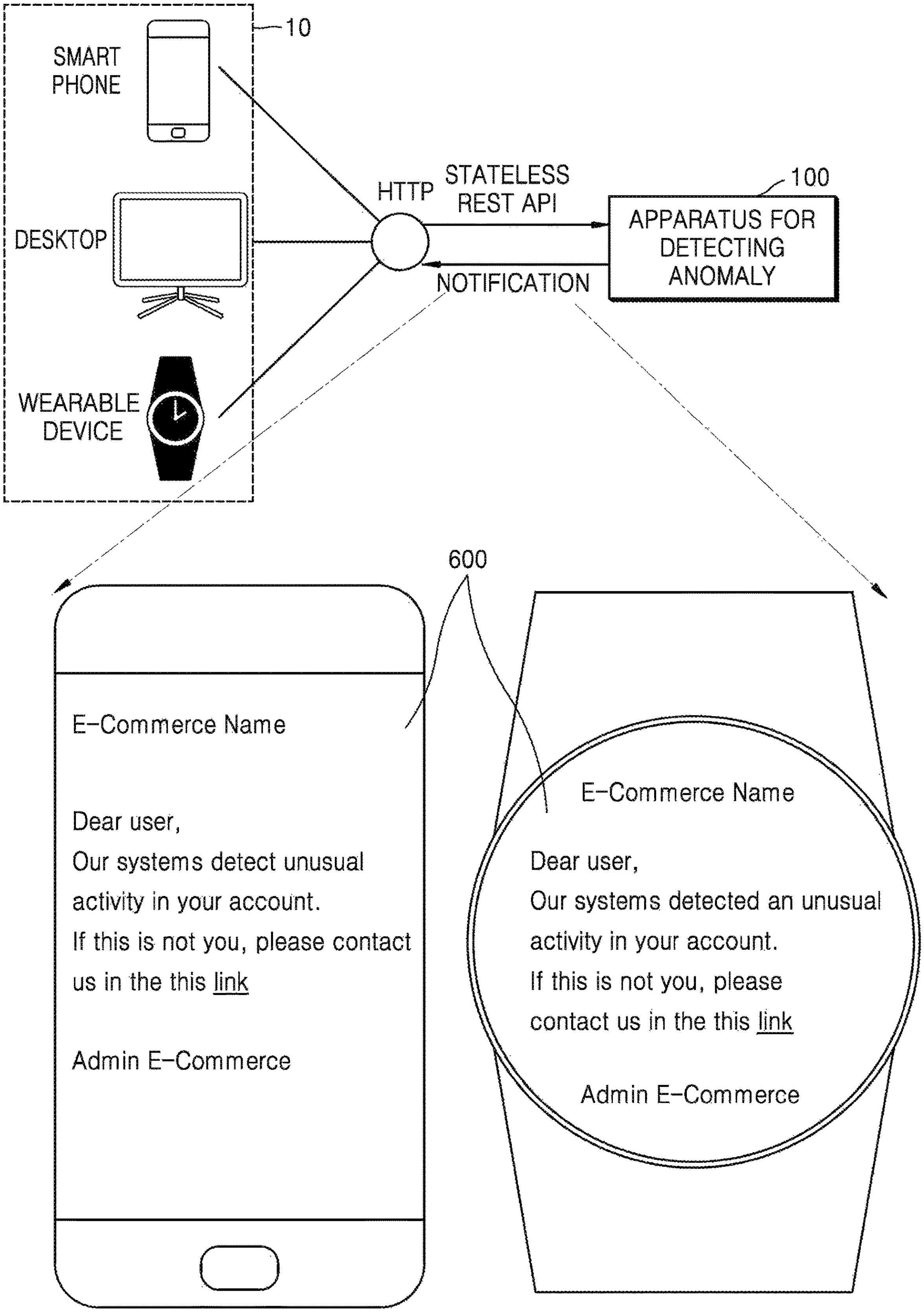
FIG. 6 shows a feedback scenario provided to a user according to an example embodiment when a system for detecting an anomaly detects a suspicious activity in a transactional application.

FIG. 6 shows a feedback scenario provided to a user according to an example embodiment when a system for detecting an anomaly detects a suspicious activity in a transactional application.

Due to a rapid increase in the adoption of smart devices (e.g., smart phones and wearable devices), numerous applications have been developed for smart phones and wearable devices, and mobile e-commerce has grown rapidly.

Referring to FIG. 6, an apparatus for detecting an anomaly may detect a suspicious activity and then immediately transmit a notification through e-mail and/or short message service (SMS) to obtain a quick response from a user. The notification may be a message 600 that reads, for example, "Our systems detected an unusual activity in your account. If this is not you, please contact us using this link." A notification for another transactional application (e.g., a bank transaction application, etc.) may be similar to FIG. 6 because the output and the type of the application is the same.

Figure 7:
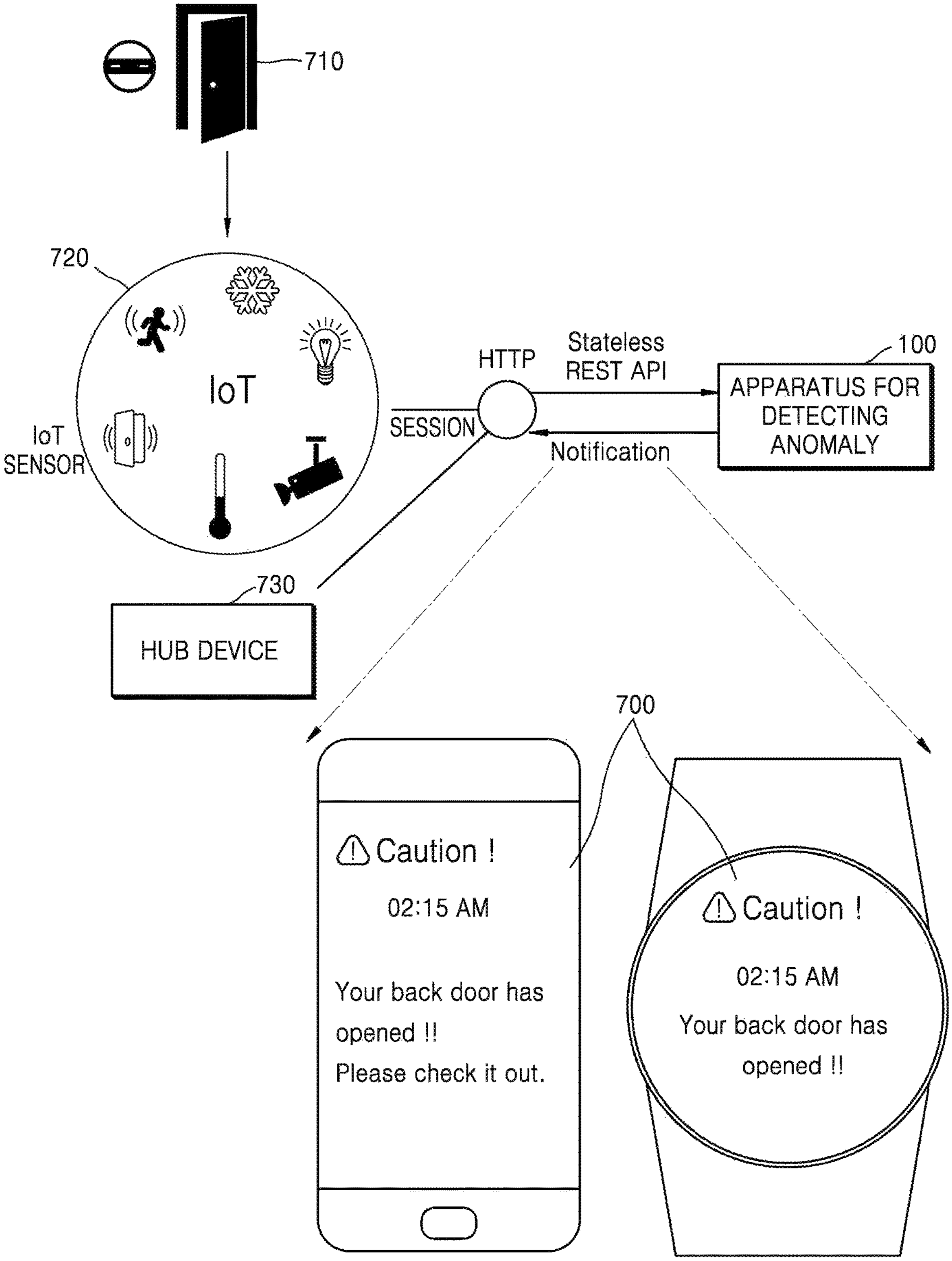
FIG. 7 shows a sample scenario in which when a system for detecting an anomaly senses an anomalous pattern, a house owner is notified of the anomalous pattern according to an example embodiment.

FIG. 7 shows a sample scenario in which, when a system for detecting an anomaly senses an anomalous pattern, a house owner is notified of the anomalous pattern according to an example embodiment.

The system for detecting an anomaly may be implemented for smart home scenarios by learning patterns of home activities according to time and place.

Referring to FIG. 7, one or more of IoT sensors 720 may sense an abnormal activity 710 of opening a back door of a house at 2 AM in the morning. When the system is combined with a night vision camera as well as a presence/motion sensor, the homeowner may obtain additional information that helps him or her to determine an appropriate next operation. Each sensor (e.g., a front door, the back door, lamps, an air conditioner (AC), windows, etc.) of IoT devices may be connected to a hub device 730 at which each sensor triggers an API call.

For example, the hub device 730 may generate an API call for transferring time information and back door sensor identification information and transmit the API call to the apparatus 100 for detecting an anomaly.

The apparatus 100 for detecting an anomaly may determine whether the currently received API call is anomalous using only data considered as API calls according to patterns of previously received data. For example, when time information transmitted from API calls and time information in the back door sensor identification information are mainly times before 10 PM according to historical data stored in a database but time information transmitted from a current API call is 2 AM in the morning, the current API call may be determined to deviate from an existing historical pattern.

Therefore, the apparatus 100 for detecting an anomaly may transmit a notification 700 that reads, "02:15 AM. Your back door was opened. Please check it out," to a user through a message and the like.

Figure 8:
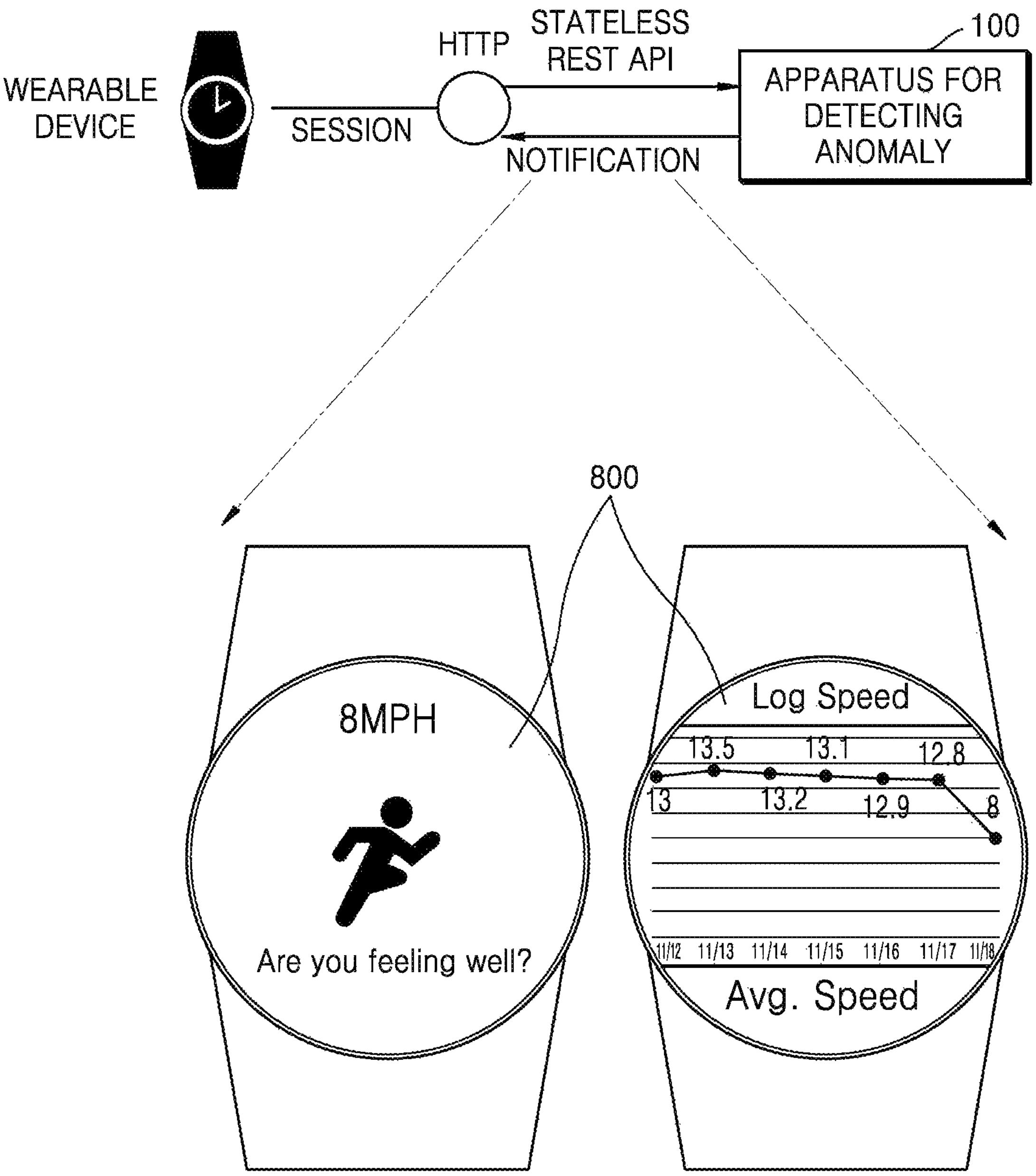
FIG. 8 shows a sample scenario in which when a jogging speed tracker/sensor senses an anomalous average speed, a system for detecting an anomaly detects an anomalous pattern and notifies a user of the anomalous pattern according to an example embodiment.

FIG. 8 shows a sample scenario in which when a jogging speed tracker/sensor senses an anomalous average speed, a system for detecting an anomaly detects an anomalous pattern and notifies a user of the anomalous pattern according to an example embodiment.

Referring to FIG. 8, a jogging application being executed in a wearable device may transmit an API call for transferring jogging speed data to the apparatus 100 for detecting an anomaly based on GPS sensor information. The apparatus 100 for detecting an anomaly may detect an anomalous speed log for the jogging application. Also, the apparatus 100 for detecting an anomaly may record a time for which a user jogs and simultaneously check a heart rate and other health conditions of the user. When an anomalous pattern or value is detected, the apparatus 100 for detecting an anomaly may report the anomalous pattern or value to a user terminal. The application may also report one or more sensor values (e.g., a GPS position and an altitude) such that more comprehensive information may be obtained.

For example, assuming that the user has a historical pattern of running at a general altitude and a first speed and running at a higher altitude and a second speed lower than the first speed, when the user running to a higher altitude decreases in speed, this is a normal situation and may not be detected as an anomaly. However, when an API call representing information of running at the general altitude and the second speed is received, the apparatus 100 for detecting an anomaly may determine that the API call has deviated from the historical pattern and detect an anomaly.

When an anomaly is detected, the apparatus 100 for detecting an anomaly may transmit, for example, a message, "Are you feeling well?" or information 800 about the user's jogging speed to the user terminal.

Figure 9:
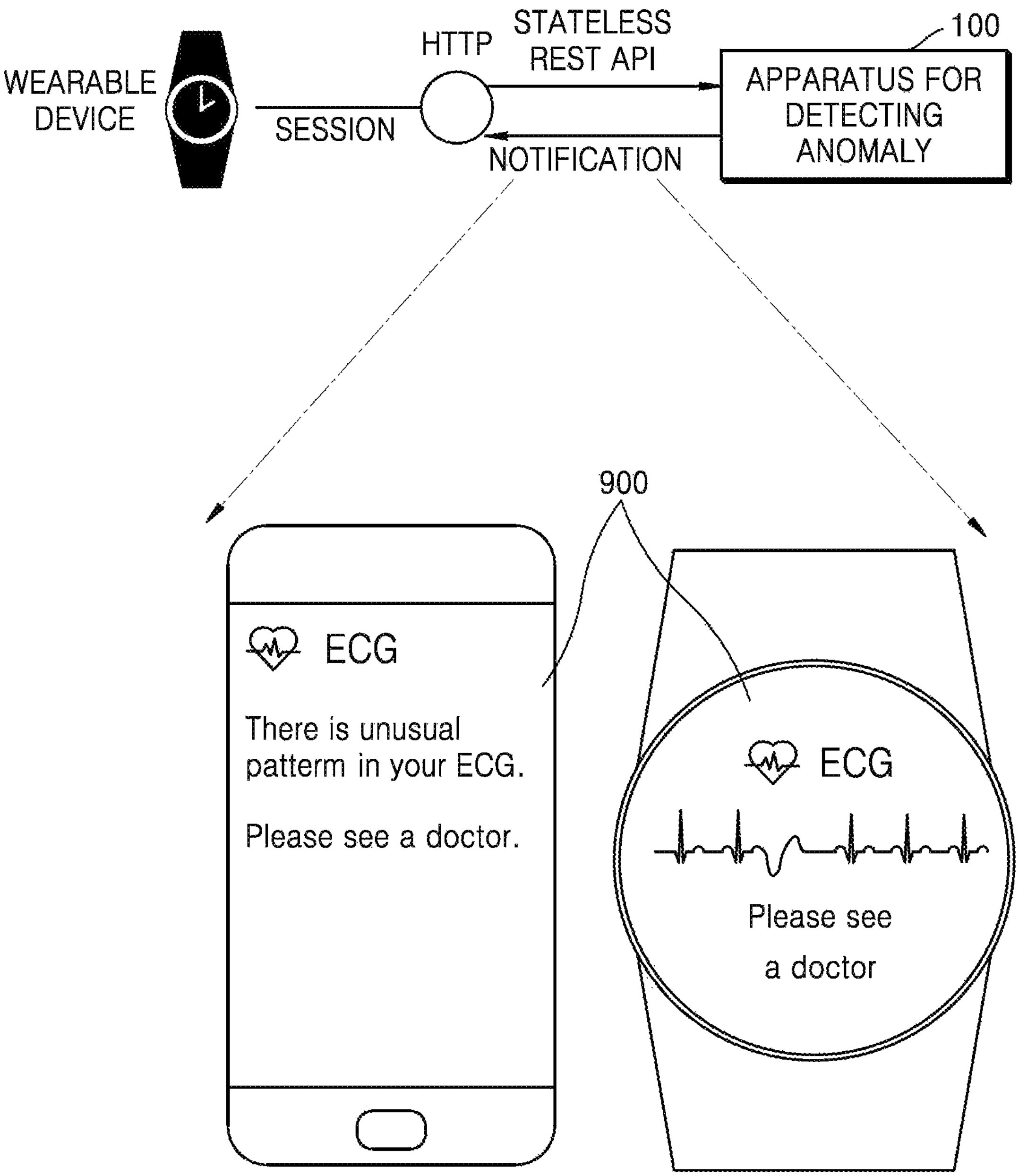
FIG. 9 shows a sample scenario in which a system for detecting an anomaly senses an anomalous pattern of a user's electrocardiogram (ECG) according to an example embodiment.

FIG. 9 shows a sample scenario in which a system for detecting an anomaly senses an anomalous pattern of a user's electrocardiogram (ECG) according to an example embodiment.

Development using wearable sensors for health monitoring has been increasing in last few years. Sensors may be used to measure some vital signs (e.g., an ECG, a heart rate, a blood pressure, etc.) for a disease management and preventive health monitoring system.

Referring to FIG. 9, an example embodiment uses an ECG monitoring system that records a user's ECG. The apparatus 100 for detecting an anomaly reads and extracts a pattern of the user's ECG. When there is an abnormal pattern in the user's ECG, an application notifies the user of the abnormal pattern. The system may provide different types of notifications according to situation.

For example, in a non-emergency situation, that is, when there is no immediate threat of death or serious injury, the apparatus 100 for detecting an anomaly may provide a notification 900 of the situation to the user.

For example, in an emergency situation, for example, when the user is unconscious, the apparatus 100 for detecting an anomaly may transmit a notification of the situation to other people, for example, the user's friends or family, a doctor, or a hospital, find an accurate location of the user using GPS, and also transmit the location.

Figure 10:
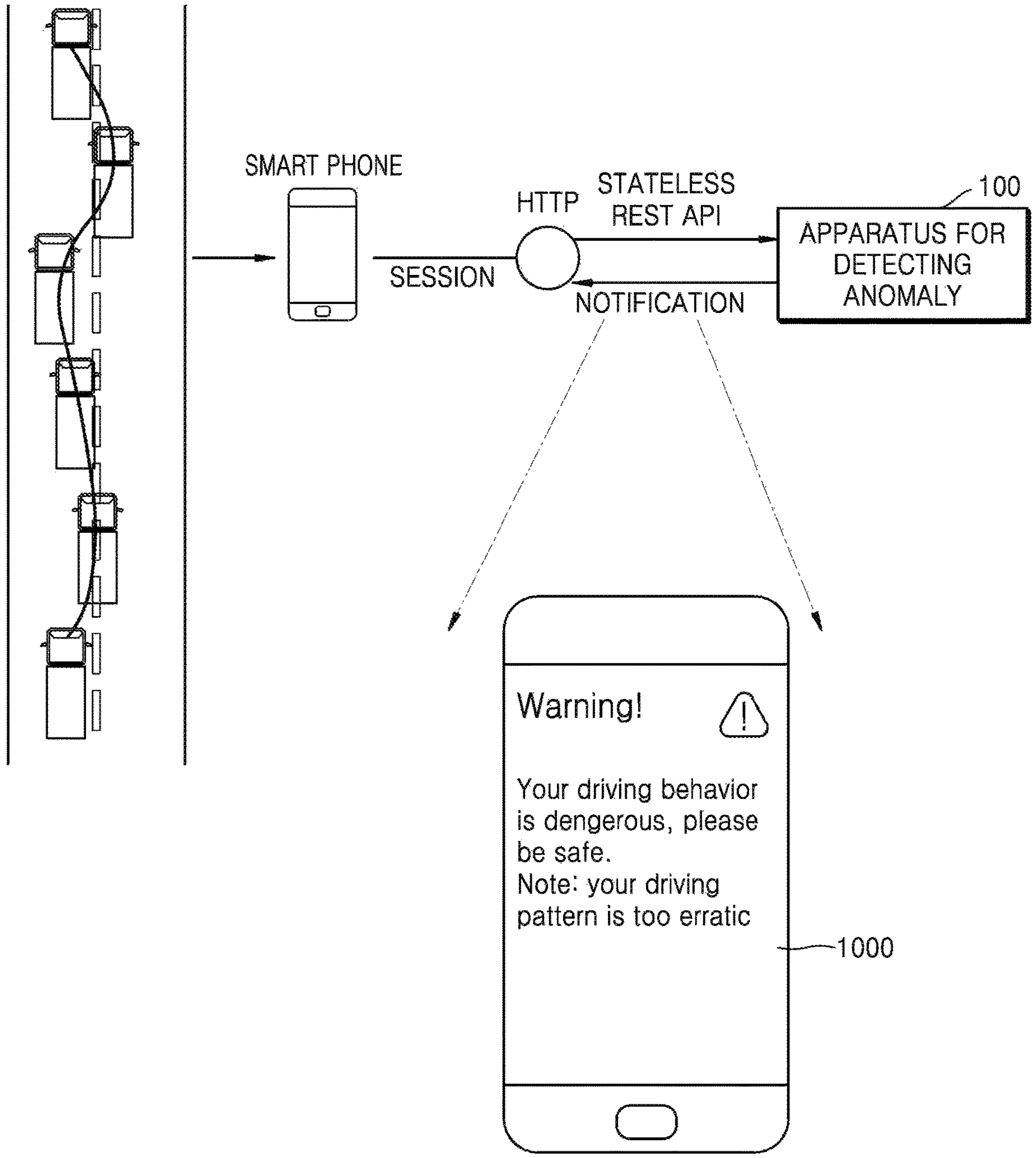
FIG. 10 shows a sample scenario in which a system for detecting an anomaly detects that a driver carelessly drives a car through a global positioning system (GPS) sensor according to an example embodiment.

FIG. 10 shows a sample scenario in which a system for detecting an anomaly detects that a driver is carelessly driving a vehicle through a GPS sensor according to an example embodiment.

Referring to FIG. 10, a sample scenario of a case in which a GPS sensor detects careless driving of a driver is shown. As shown in FIG. 10, a system for detecting an anomaly may be applied to the transportation field to observe behavior of a driver. The system extracts track information of a vehicle using a GPS sensor and then determines whether behavior of the driver is safe or dangerous. When the track information of the vehicle driven by the driver deviates from a pattern of historical data stored in a database, the apparatus 100 for detecting an anomaly may transmit a message 1000, "Your driving behavior is dangerous. Please be careful," to a user terminal.

Figure 11:
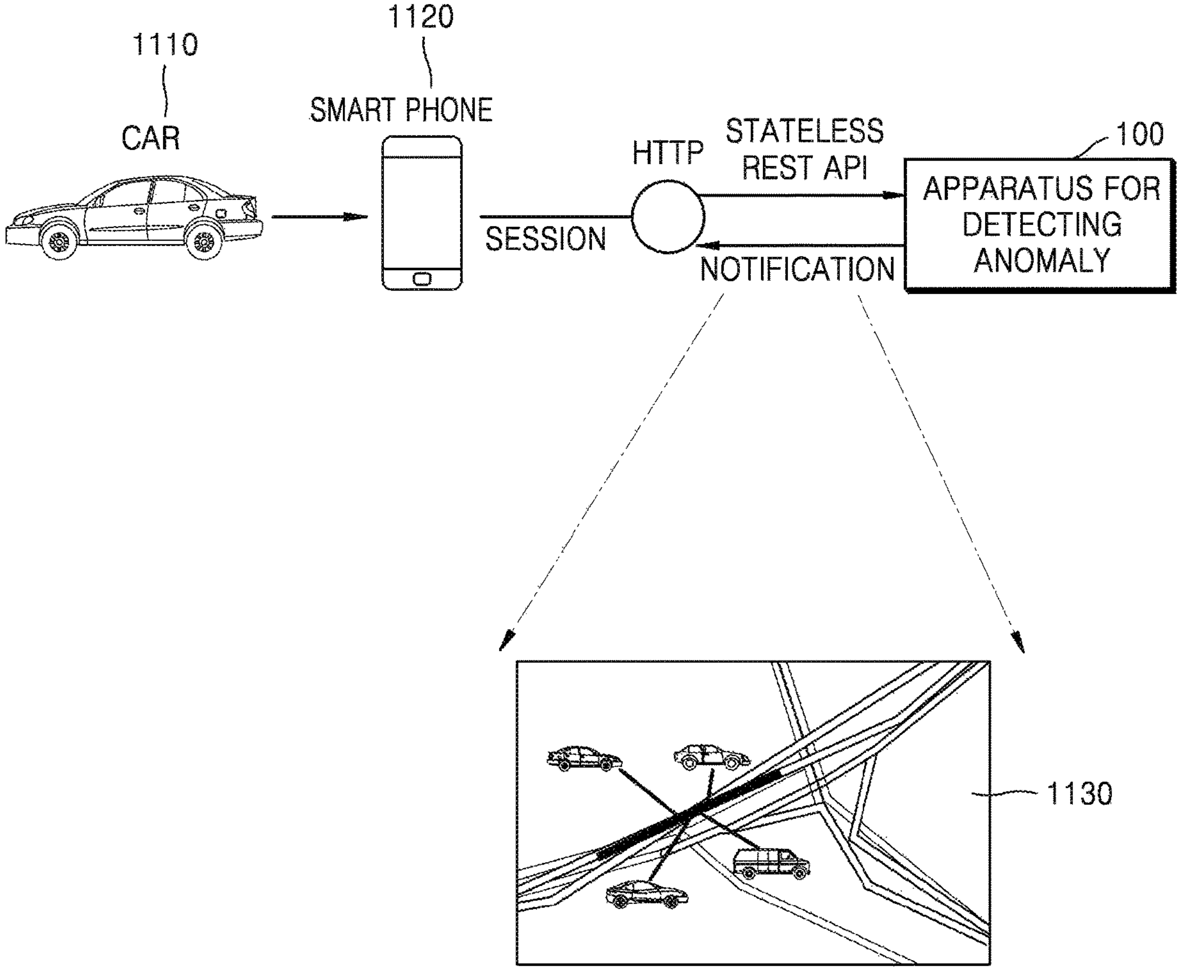
FIG. 11 shows a sample scenario in which a system for detecting an anomaly provides road information according to an example embodiment.

FIG. 11 shows a sample scenario in which a system for detecting an anomaly provides road information according to an example embodiment.

Referring to FIG. 11, when the present disclosure is implemented for traffic reporting, a congested road may be considered an anomalous situation. A GPS sensor of a car 1110 or a smart phone 1120 may detect traffic information, such as a location of a road, a speed of vehicles on the road, and the like, and the car 1110 or the smart phone 1120 may transmit an API call for transferring the detected traffic information to the apparatus 100 for detecting an anomaly. The apparatus 100 for detecting an anomaly may compare a data pattern of the received API call with a stored data history, and detect an anomaly when the data pattern of the API call deviates from the stored data history. Here, the anomaly may represent the highly congested road condition. The apparatus 100 for detecting an anomaly may provide a feedback 1130 indicating that the road is highly congested to terminal devices of other users as well as a terminal device that has transmitted the API call. The feedback information may be spread to other drivers such that others may avoid the area and look for alternative routes.

A sample scenario in which an apparatus for detecting an anomaly provides a door lock notification of a smart house according to an example will be described with reference to FIGS. 12 to 14. The apparatus for detecting an anomaly may be implemented for a smart home by learning patterns of home activities.

Figure 12:
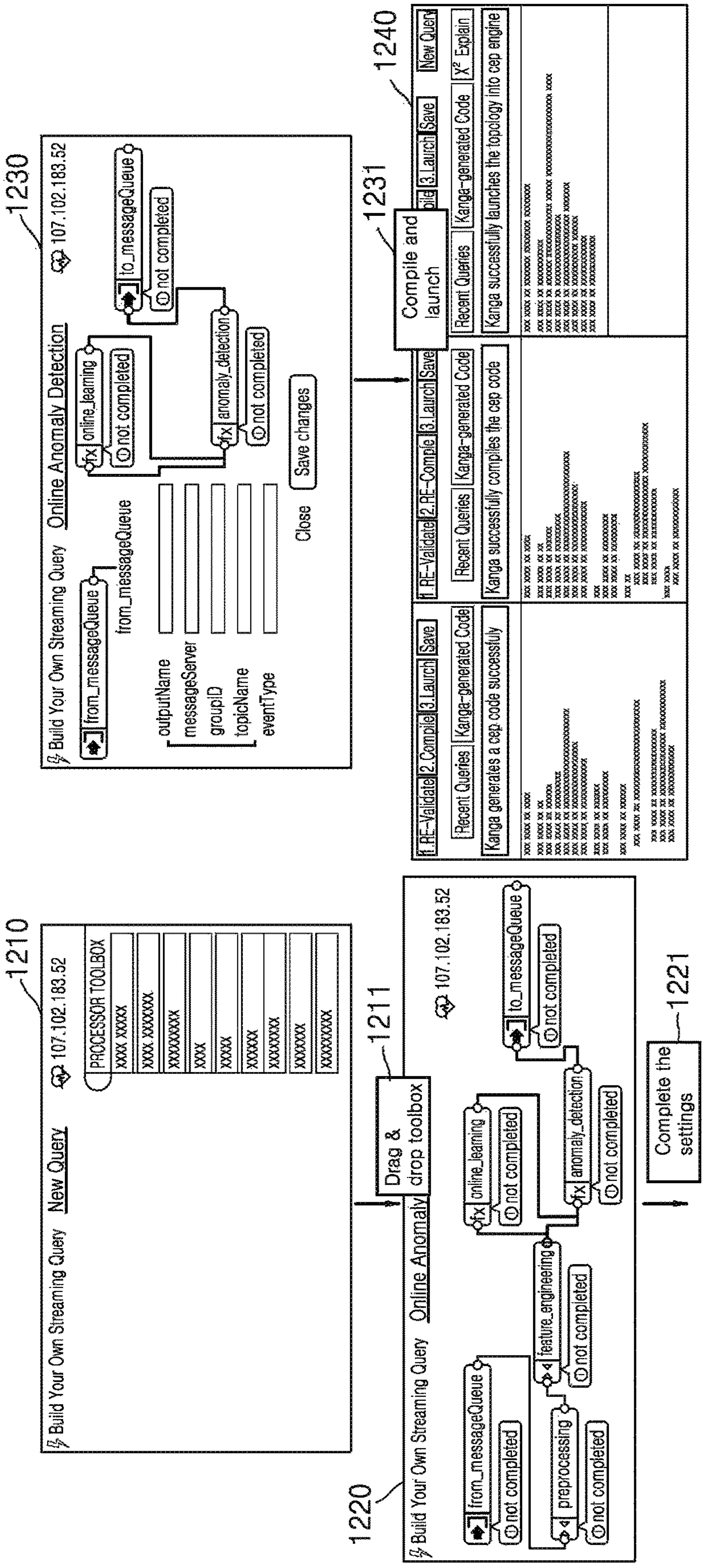
FIGS. 12, 13, and 14 show sample scenarios in which a system for detecting an anomaly provides a notification of a door lock of a smart house according to an example embodiment.
Figure 13:
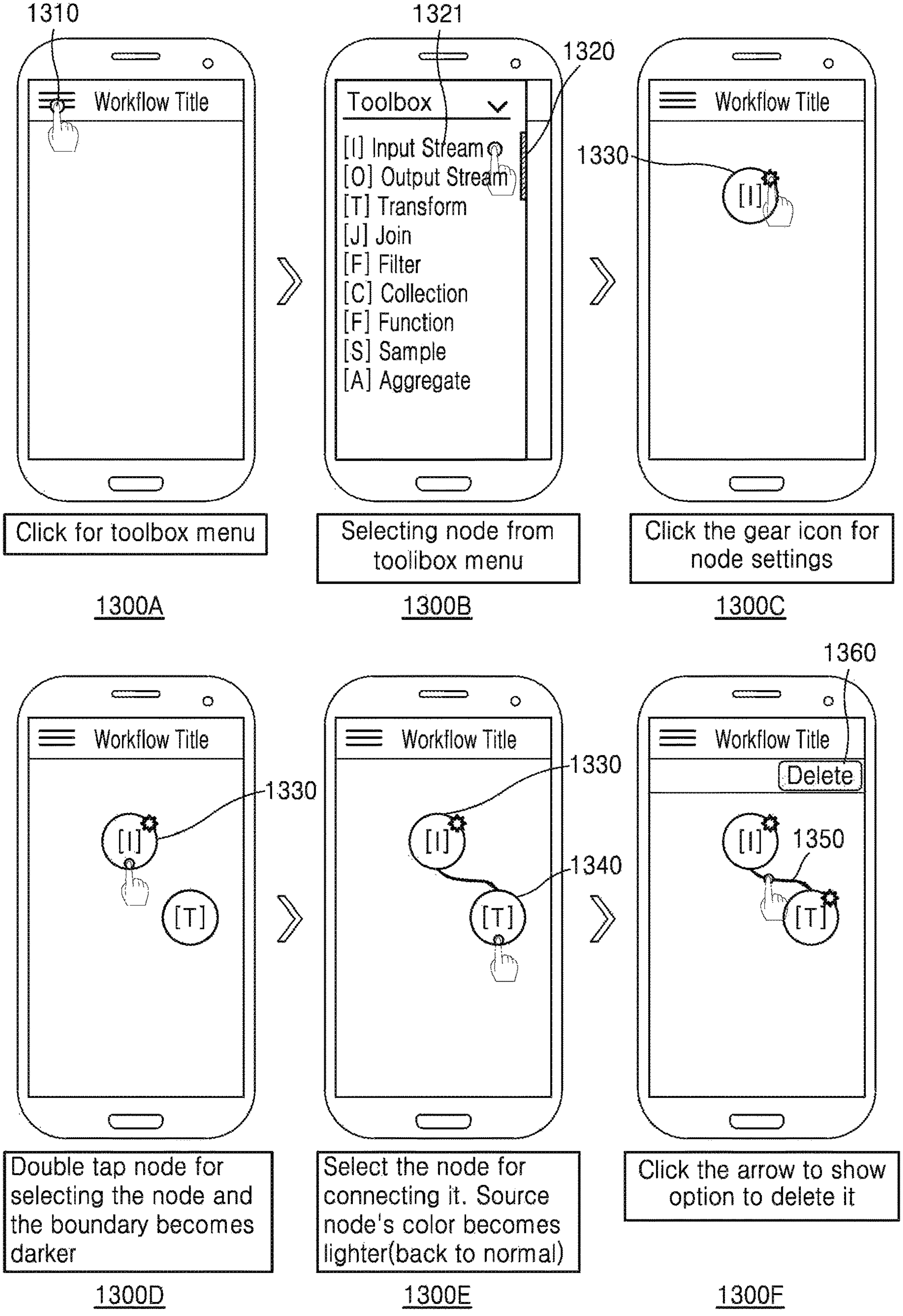
Figure 14:
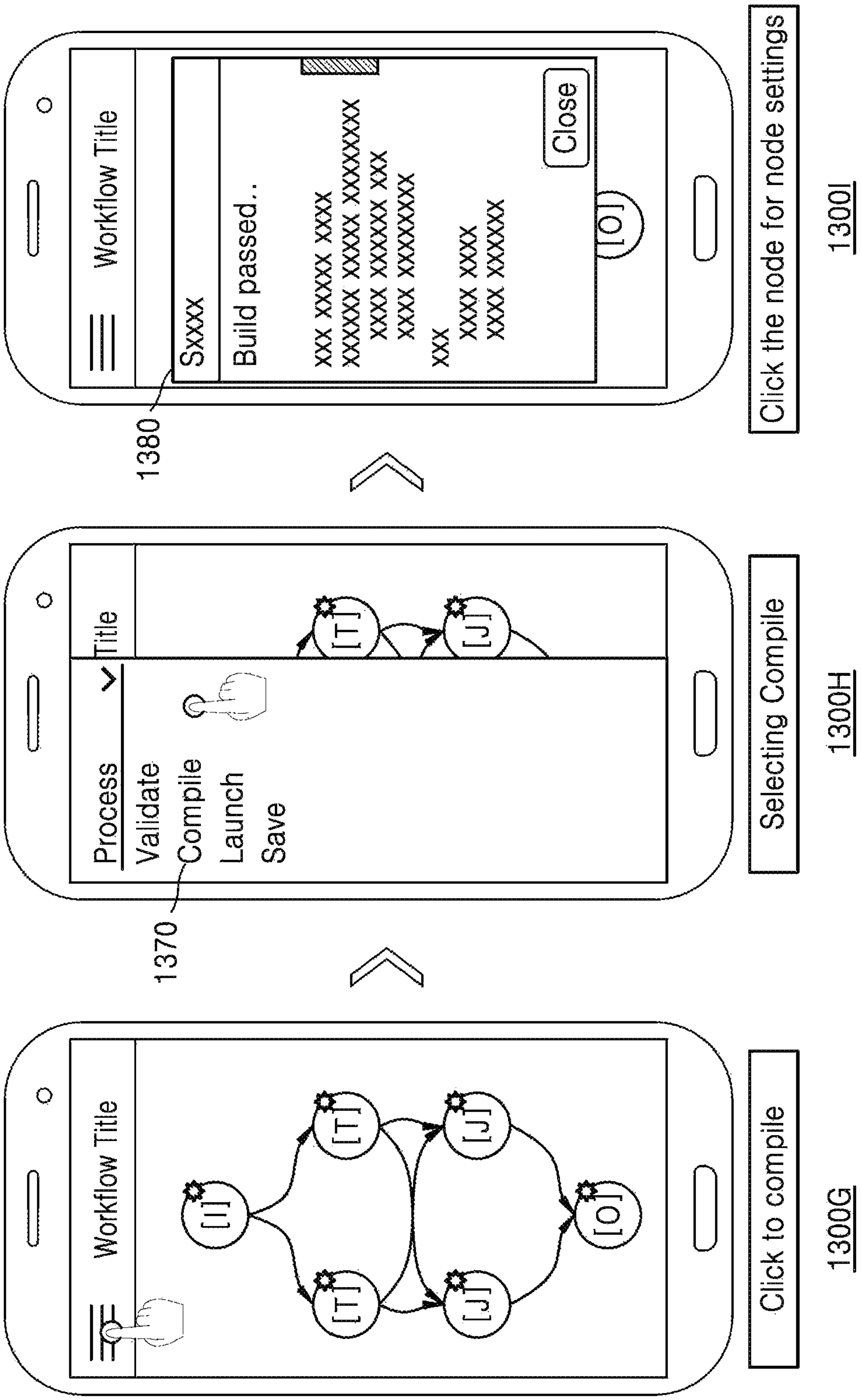

FIGS. 12 to 14 show workflows for building a stream-processing workflow designer. As shown in FIG. 12, a user may easily build and maintain his or her system by building a stream-processing workflow. A processor toolbox in a workspace for building a stream-processing workflow includes many modules. A user may connect one process to another process by dragging and dropping a module. Before a workflow is compiled and launched, each process setting needs to be completed.

In each operation, a user/administrator may use various options required to build a whole system by processing input data, preprocessing data, formatting data, extracting information, generating a predictive model, and implementing an anomalous event detection module.

1210 of FIG. 12 shows a welcome page of a workflow designer with a processor toolbox including all tools required for building a system.

1220 of FIG. 12 shows an example of building a workflow using a workflow designer run by drag-and-drop 1211.

1230 of FIG. 12 shows an example in which an administrator fills settings 1211 of individual nodes after dragging the nodes.

1240 of FIG. 12 shows that the workflow is compiled (1231) when the settings are completed, and in this operation, the administrator may see information about whether the workflow has been successfully compiled and a topology is launched.

FIGS. 13 and 14 show an example of a mobile version of a stream-processing workflow.

Referring to FIGS. 13 and 14, when a user clicks a toolbox menu icon 1310 in 1300A, a toolbox menu 1320 is displayed in a mobile terminal as shown in 1300B. When the user selects one node item 1321 in the toolbox menu 1320, a selected node 1330 is displayed as shown in 1300C, and the user may click the node 1330 for node setting.

When the user double-taps the node 1330 for node selection in 1300D, the boundary of the node may be highlighted (e.g., displayed darker). When the user selects a node 1340 to connect the node 1330 to the node 1340 in 1300E, the boundary color of the source node 1330 returns to the original color. When the user clicks an arrow 1350 in 1300F, an option 1360 for deleting the arrow 1350 is displayed.

After completing node setting and connection in 1300G of FIG. 14, the user clicks a compile icon 1370 in 1300H. Then, after compiling, a compile success message 1380 may be displayed as shown in 1300I.

A sample user interface of a data browser module will be described with reference to FIGS. 15 and 16.

Figure 15:
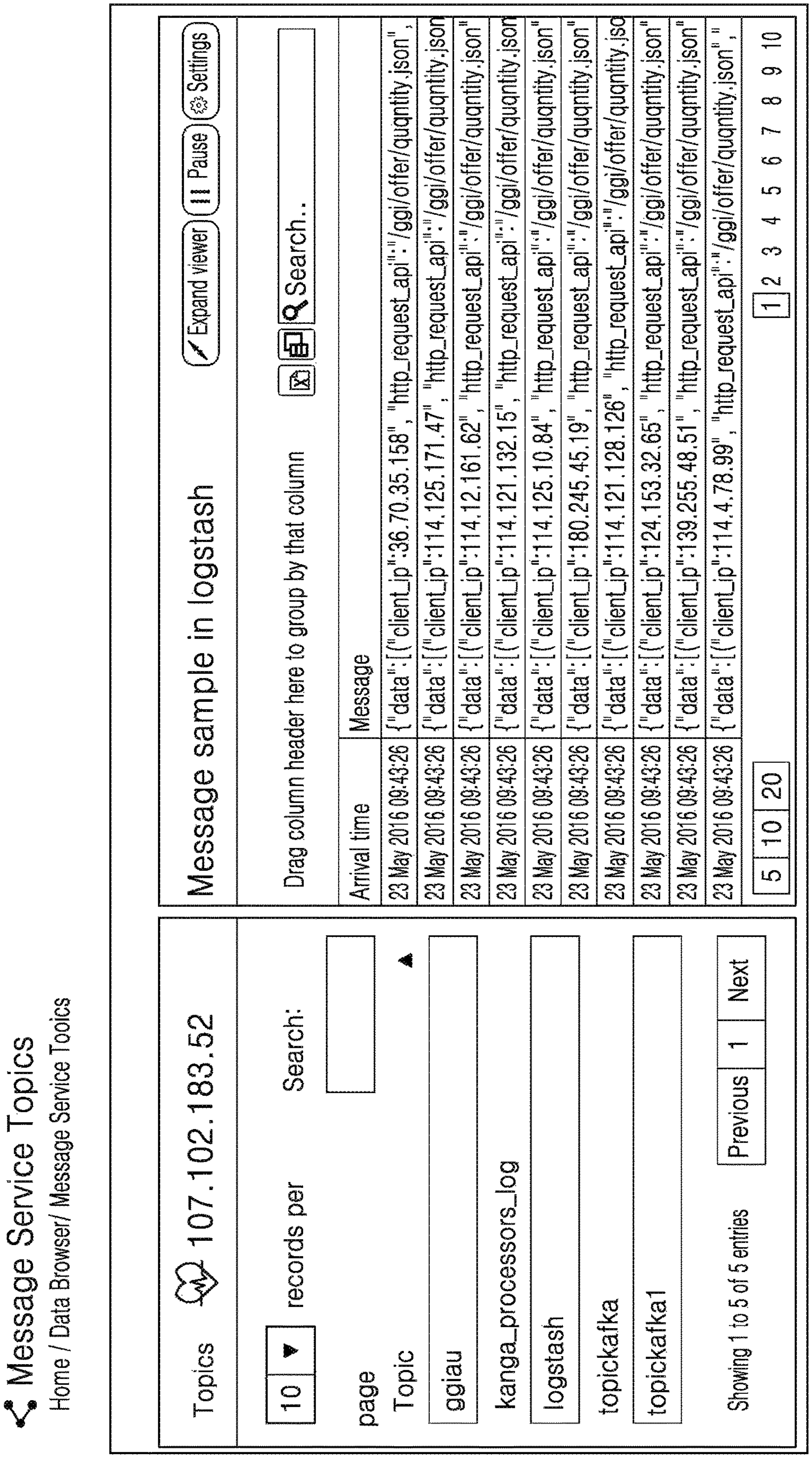
FIGS. 15 and 16 show sample user interfaces of a data browser module according to an example embodiment.
Figure 16:
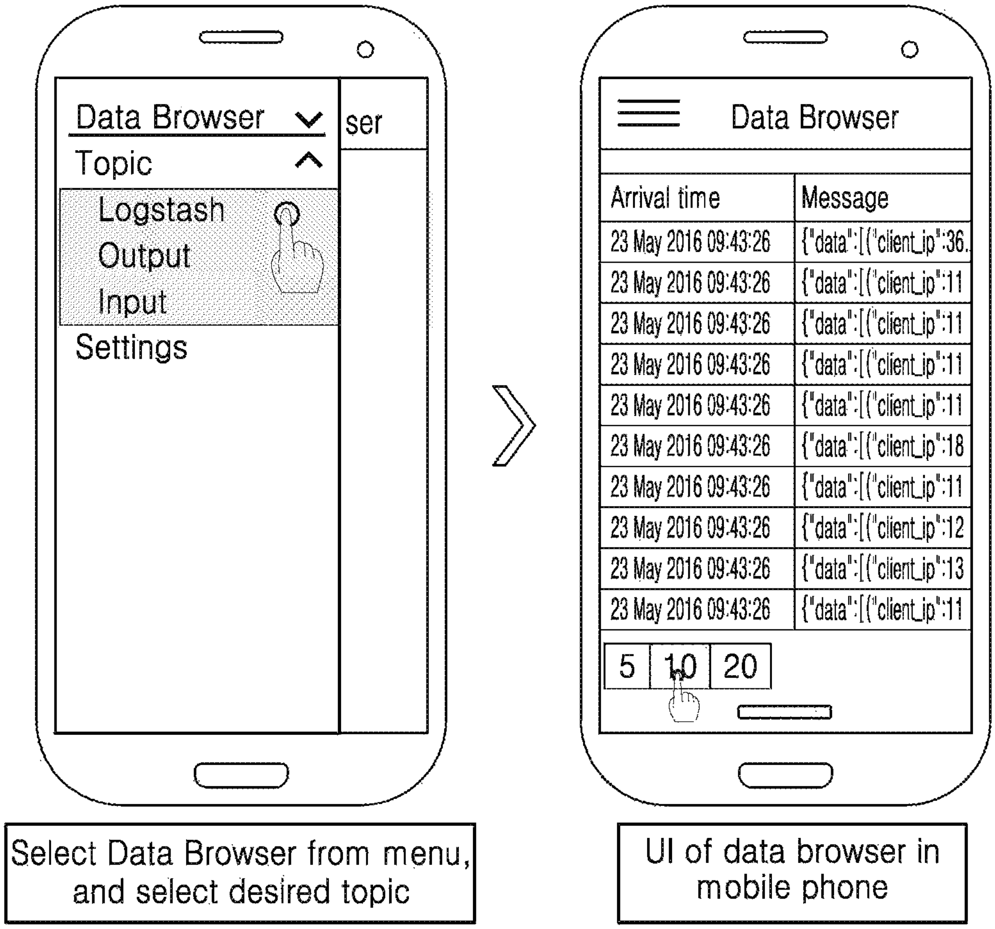

As shown in FIG. 15, a data browser functions to show details of data including new incoming streaming data. The data browser organizes data of each topic. The data browser also supports keyword searches and data forwarding. A user interface of a data browser for mobile version is shown in FIG. 16.

Figure 17:
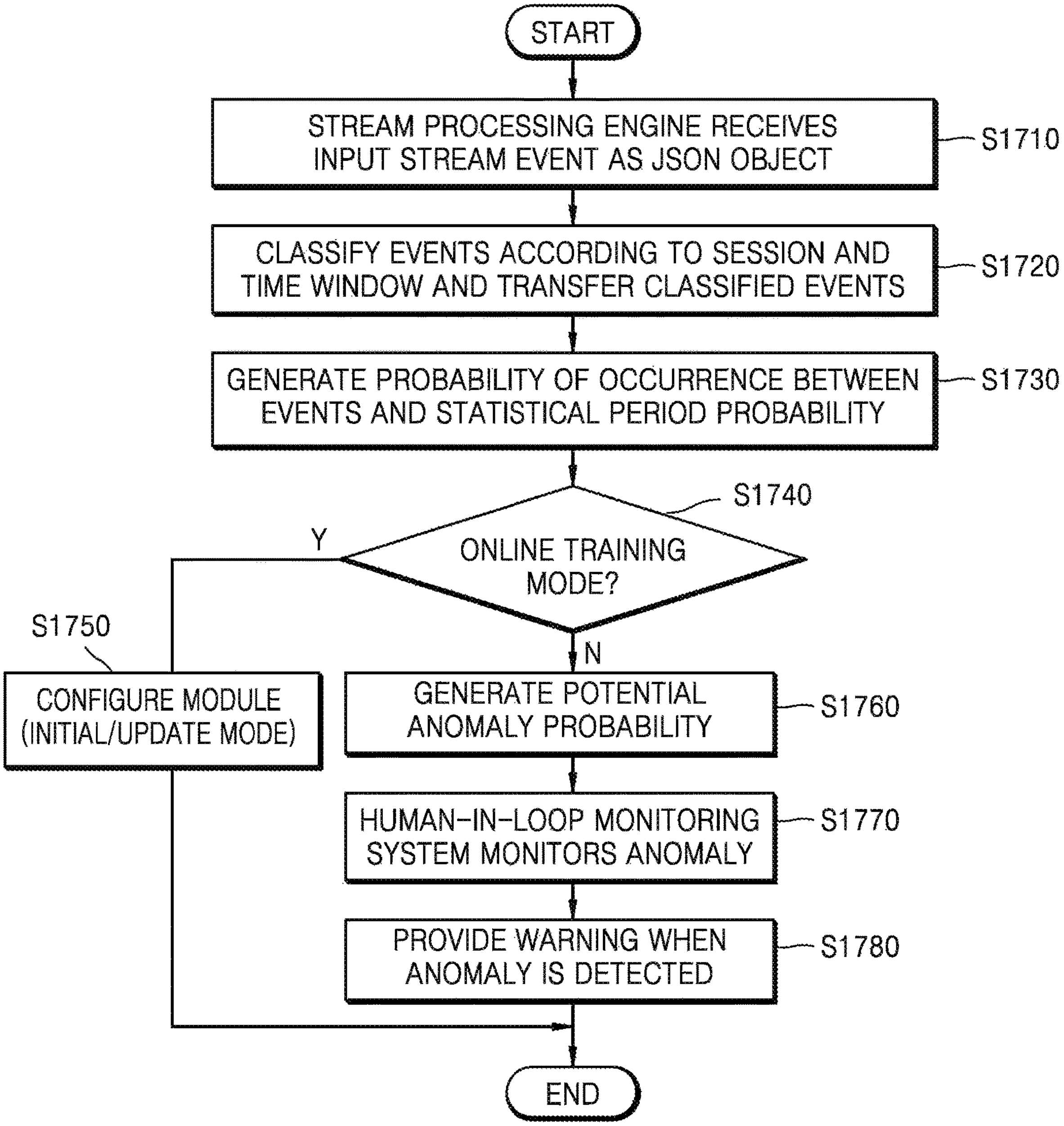
FIG. 17 is a flowchart illustrating operation of an anomaly detection process according to an example embodiment.

FIG. 17 is a flowchart illustrating operation of an anomaly detection process according to an example embodiment.

Referring to FIG. 17, in operation S1710, a stream processing engine receives an input stream event as a JavaScript Object Notation (JSON) object.

Since input data streams may be collected from different devices and different applications, the stream processing engine may perform transactional data processing/sensing data processing according to input data.

In operation S1720, the stream processing engine may classify events according to session and time window and transfer the classified events to an anomaly detection module.

In operation S1730, the anomaly detection module may generate a probability of occurrence between events and a statistical period probability.

In operation S1740, the anomaly detection module may determine whether it is in an online training mode.

In operation S1750, when it is in the online training mode, the anomaly detection module may configure a model. This system may learn and process streaming data. At first, an initial model is built based on prior knowledge of data, and may be updated by continuously learning new incoming data. Also, an administrator may check potential anomalous data advised by the system and label the potential anomalous data as anomalous data. The label may be used as ground truth for further improving the model.

In operation S1760, when it is not in the online training mode, the anomaly detection module may generate a potential anomaly probability.

In operation S1770, the anomaly detection module may monitor anomalies.

In operation S1780, the anomaly detection module may provide a warning when an anomaly is detected.

FIG. 18 shows samples of a relative entropy matrix as a feature.

Feature engineering functions to represent input data based on a nature type.

To process a transactional application, a relative entropy matrix and time information are used as features. There are many application features in a transactional application. A user may explore the application features using a REST API. In example embodiments, a user's activity is defined based on a REST API coming to a server. It is possible to define the user's jump from one feature to another feature. In other words, some users may prefer a particular feature(s), and some other users may not prefer the particular feature(s). A relative entropy matrix is used to define a probability of occurrence of an API call, and the probability may be later defined by an operation of a user.

FIG. 18 shows an example of a relative entropy matrix of features, which is fed to an anomaly detection algorithm. In given API call data, 1810 of FIG. 18 shows an example of a normal session, and 1820 of FIG. 18 shows an example of an abnormal session. FIG. 18 shows that the normal session actively explores and hits more API calls than the abnormal session. Due to a probability of D(A||B)≠D(B||A), Kullback-Leibler (KL)-divergence is used to define a relationship between APIs. Using a relative entropy matrix, it is tried to check a pair relationship between API calls. To obtain more information, statistic time behavior may be added to features such that time information may be obtained. After the relative entropy matrix and statistical information of a user's time are combined, historical information is generated, and representation learning may be used to label a sequence.

Figure 19:
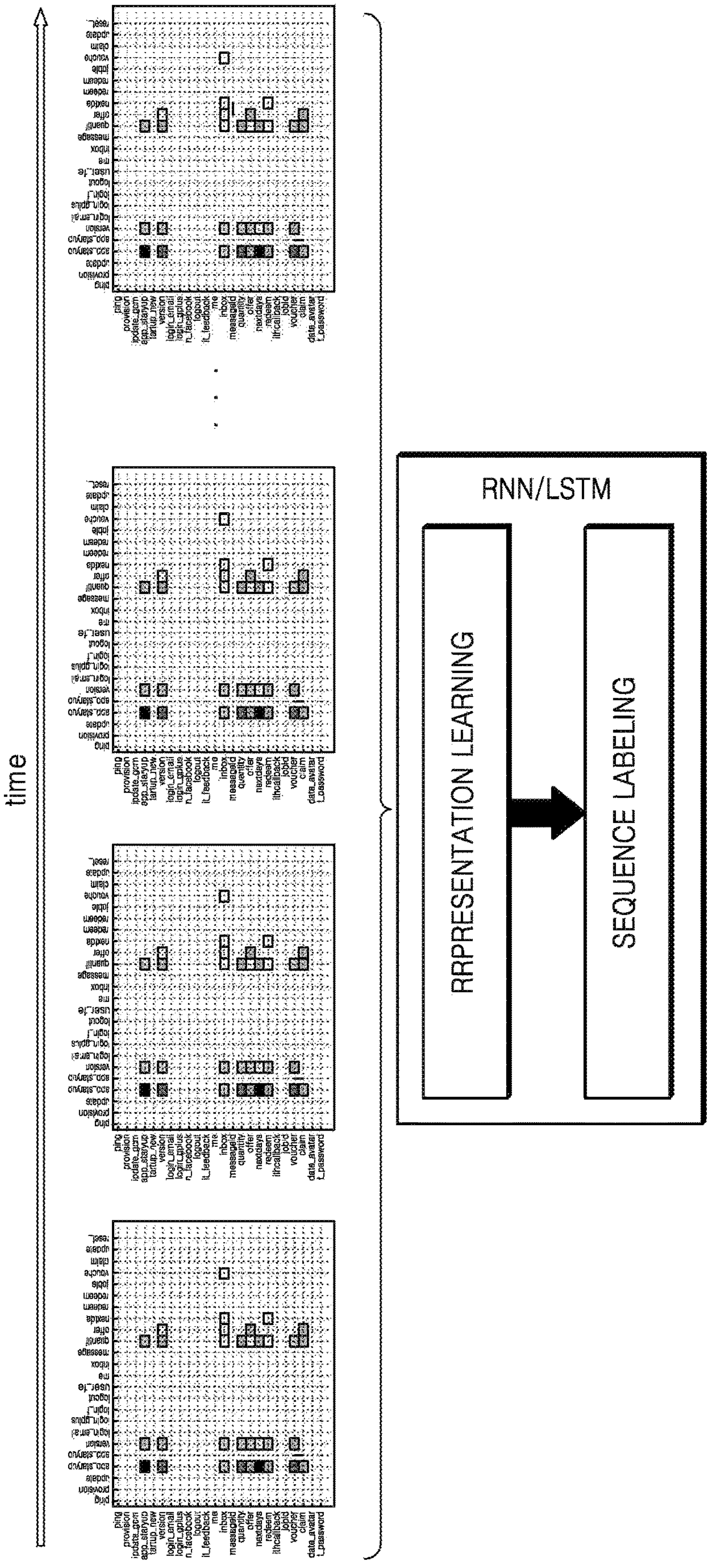
FIG. 19 shows a sequence labeling method of a system for detecting an anomaly.

FIG. 19 shows a sequence labeling method of a system for detecting an anomaly.

An apparatus for detecting an anomaly attempts to learn and label a sequence from historical features.

In machine learning, feature learning or representation learning is a technology that allows a system to automatically discover representations required for feature detection and classification from raw data. Representation learning denotes learning, by a system itself, how the system needs to convert input data.

In machine learning, sequence labeling is a type of pattern recognition task that involves the algorithmic assignment of a categorical label to each member of a sequence of observed values. A common example of sequence labeling is speech tagging that assigns a part of speed to each word in an input sentence or document. Sequence labeling denotes tagging input data with a label indicating what kind of data it is, and the label becomes input data for machine learning.

When a label of a sequence is abnormal, the system may notify a user that the label is abnormal. Here, the apparatus for detecting an anomaly may use a recurrent neural network (RNN) and a long-short term memory (LSTM).

The RNN is a deep learning model for learning data that varies over time such as time-series data. The RNN is an artificial neural network (ANN) that is built by connecting a reference time point (t) and a next time point (t+1).

However, when a deep neural network (DNN) is connected to every time point, a problem that a gradient value resulting from old data vanishes (the vanishing gradient problem) makes learning difficult. A representative model for solving this problem is an LSTM RNN.

FIG. 20 shows an example of API calls for using and claiming a coupon in a loyalty program.

Referring to FIG. 20, an API call may include various kinds of information, such as an Internet protocol (IP) address, a timestamp, a hypertext transfer protocol (HTTP) verb, a message, an HTTP status code, and the like.

For example, an apparatus for detecting an anomaly may detect, as an anomaly, a user executing the program and directly claiming a coupon without inspecting the data present. The apparatus for detecting an anomaly may detect an activity of a user different from activities of many other users as an anomaly.

Figure 21:
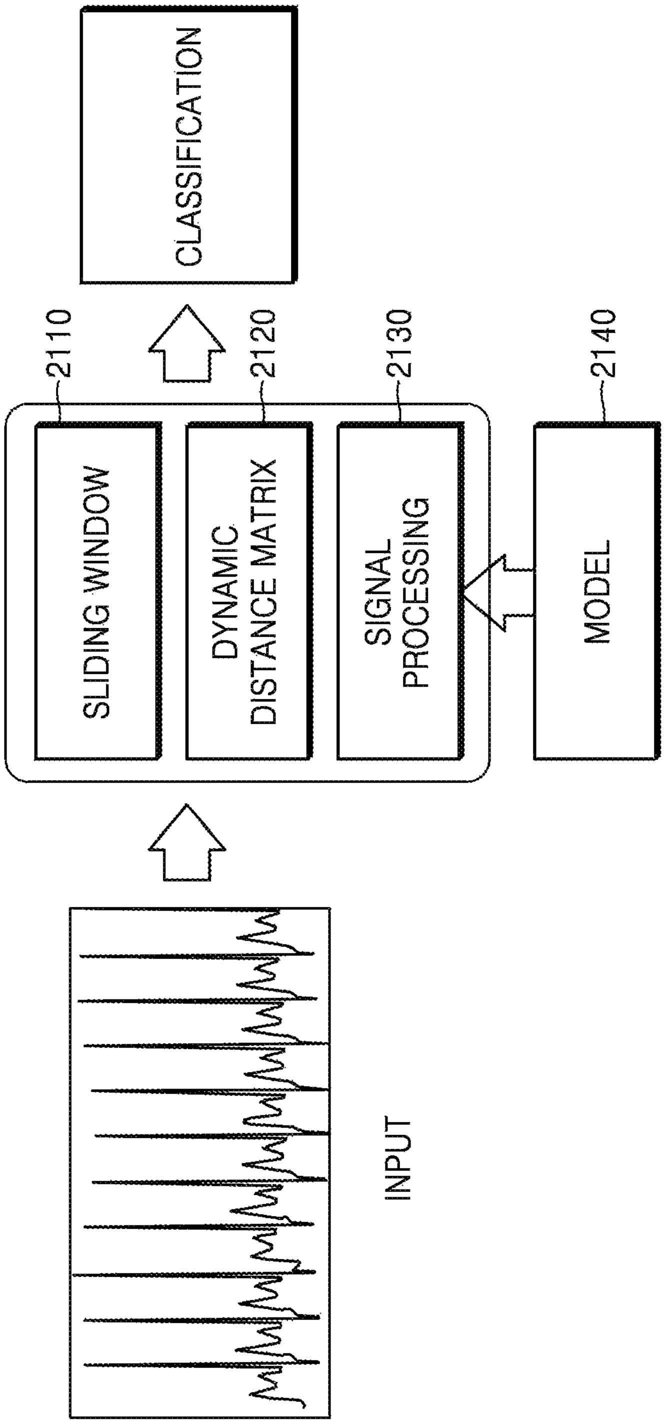
FIG. 21 shows an overview of a time-series information processing flow, in which an input signal is processed until a classification value is obtained, of a mobile sensing application according to an example embodiment.

FIG. 21 shows an overview of a time-series information processing flow of a sensing application according to an example embodiment.

Since data of a sensing application is time-series data, by defining a dynamic distance 2120 and a sliding window 2110 based on a matrix, it is possible to make feature extraction more robust even when pieces of input data do not have the same length. An input signal is processed (2130) using a model 2140 until a classification value is obtained.

Another method of processing pieces of data having different lengths involves providing subsequence data of an input for sliding window feature extraction. In a learning model, normal activity data is used to identify a normal situation overall. These days, many applications have signal outputs, such as heartbeats, pulses, and oxygen saturation, but another kind of data, such as a location (GPS), may be considered as time-series data.

A sample scenario of a human-in-loop monitoring system will be described will be described with reference to FIGS. 22 and 23.

Figure 22:
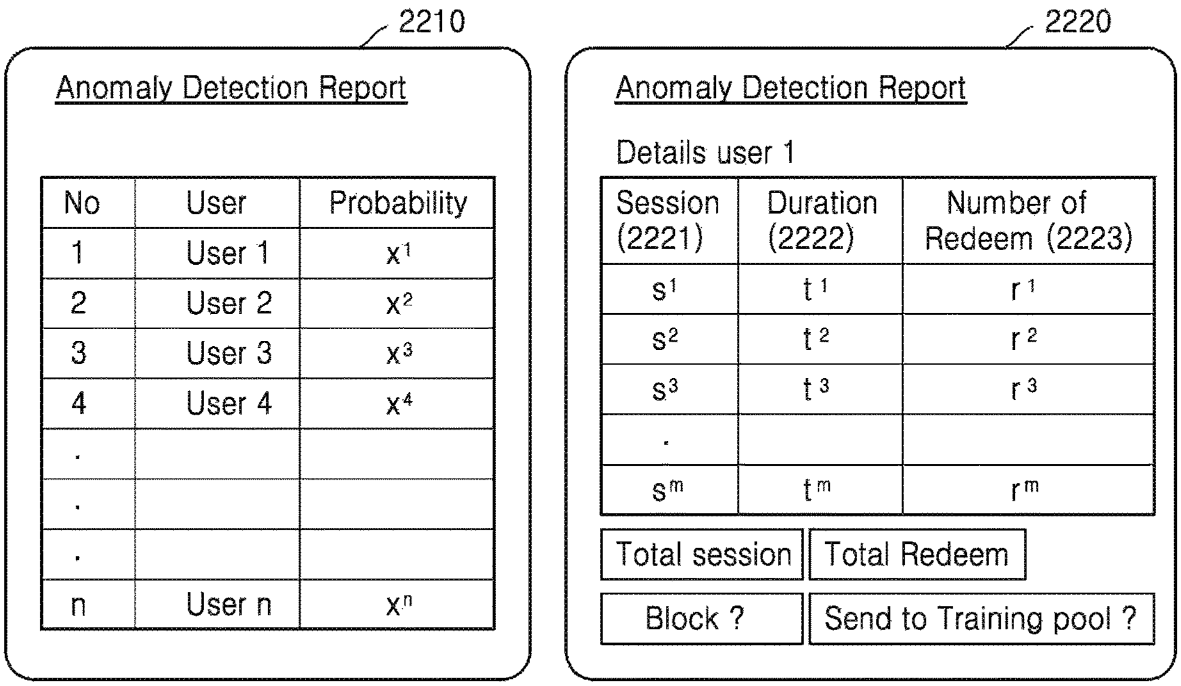
FIG. 22 shows an example of a suspicious activity list recommended by a system according to an example embodiment.

FIG. 22 shows an example of a suspicious activity list recommended by a system according to an example embodiment.

An administrator or an expert may obtain a list of suspicious activities recommended by a system on an administration panel. Based on the recommended list, the expert may observe each suspicious user and block the user when an activity of the user is deemed to be malicious or undesirable.

The list includes information on suspicious users with probability/distance values. The higher the probability value, the more suspicious a user is. The system inquires information in the list from a transactional database and obtains complete information on a suspicious user. After observing supporting information, the expert/administrator may determine that since the suspicious user actually performs a malicious activity, it is necessary to block the user so that the user may not use the application again, or may determine that the user's activity is a normal activity. Such a determination becomes a label for building a next model and makes a recommendation system more accurate.

An anomaly detection report 2210 of FIG. 22 shows a probability of each of a plurality of users. The probability denotes a probability score indicating whether an activity of the corresponding user is anomalous or not.

In the anomaly detection report 2210, details of user 1 are shown in 2220.

The details 2220 show a duration and the number of redeem corresponding to each of a plurality of sessions for user 1.

A session 2221 denotes a status unit in which a user uses an application after logging into the application. When the user logs out and then logs in again, a new session begins.

A session is a concept for maintaining a state between a client and a server. When a client makes an initial connection, a unique session ID is given to the client. The client may automatically and temporarily store the session ID in a cookie, or may append the session ID to the end of a URL when no cookie is supported. Such a session ID may be a means for identifying the corresponding client when the client makes a connection again. The session ID may be a string of an arbitrary length. The server needs to have the same session ID, and may identify the client when the client makes a request to the server with the given session ID.

A duration 2222 denotes a time between API calls of the user.

Redeeming refers to the user's use of a received coupon. When the user does not redeem the received coupon, other people may redeem the coupon. The number of redeem 2223 indicates the number of redeeming operations performed by the user for the corresponding duration.

Figure 23:
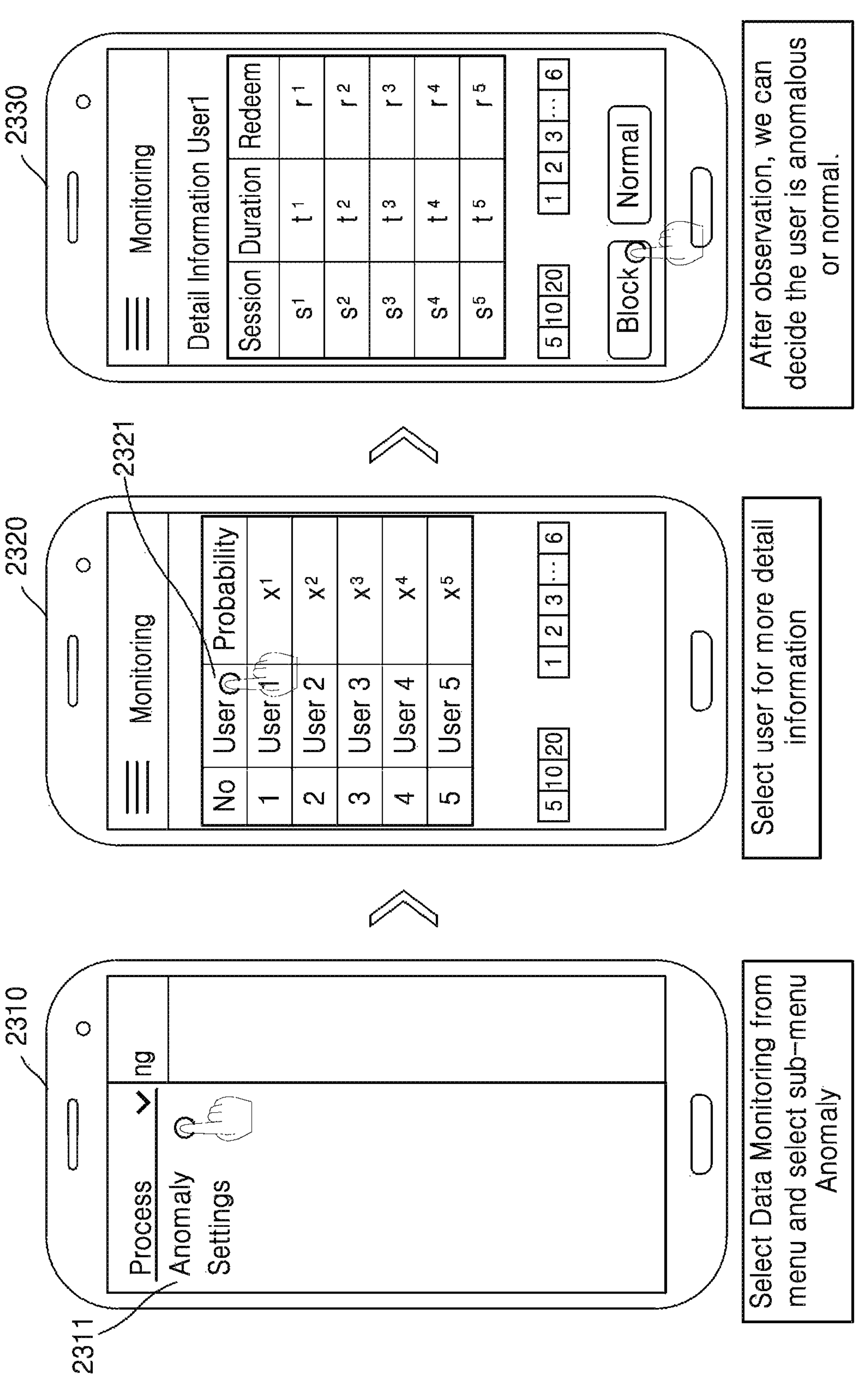
FIG. 23 shows a scenario of a mobile version of a human-in-loop monitoring system according to an example embodiment.

FIG. 23 shows a scenario of a mobile version of a human-in-loop monitoring system according to an example embodiment.

Referring to FIG. 23, in 2310, a user may select a data monitoring item from a menu and also select a submenu "Anomaly."

In 2320, the user may select an item "User 1" 2321 to obtain detailed information.

In 2330, the user may observe detailed information of user 1 and then determine whether an activity of user 1 is anomalous or normal.

Figure 24:
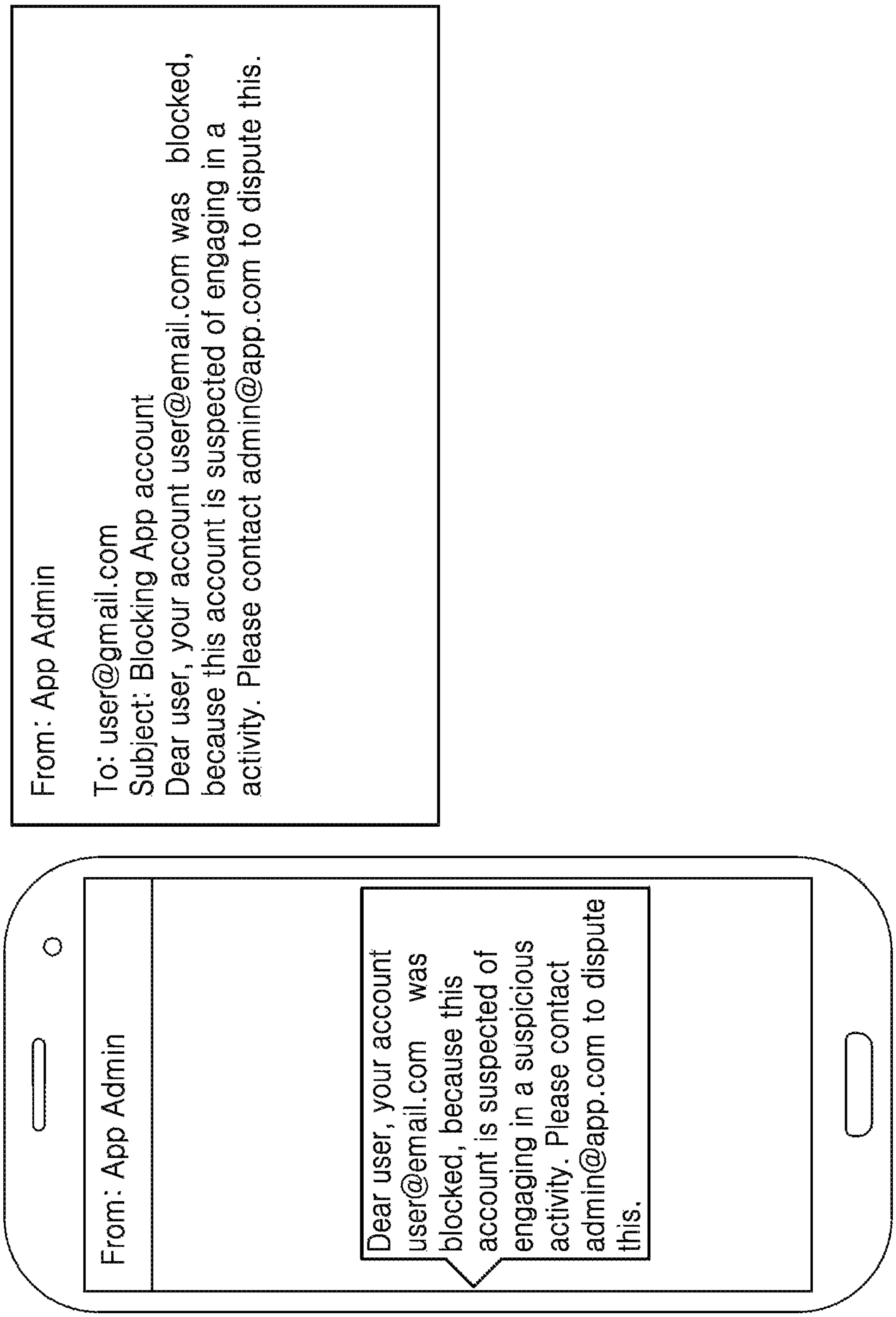
FIG. 24 shows a sample scenario in which a system for detecting an anomaly detects a suspicious activity and notifies a user of the suspicious activity according to an example embodiment.

FIG. 24 shows a sample scenario in which a system for detecting an anomaly detects a suspicious activity and notifies a user of the suspicious activity according to an example embodiment.

A response system (a user feedback) is intended to notify a user of an activity of the user who is considered to be suspicious. As shown in FIG. 24, information transmitted through an SMS or e-mail notifies a user that a corresponding activity is sensed to be suspicious and the system will block the user. When the user receiving the notification thinks that he or she did not perform a suspicious activity, he or she may contact an administrator of a corresponding application or a listed e-mail address, or review types of activities that are considered to be suspicious by the system or the administrator.

Figure 25:
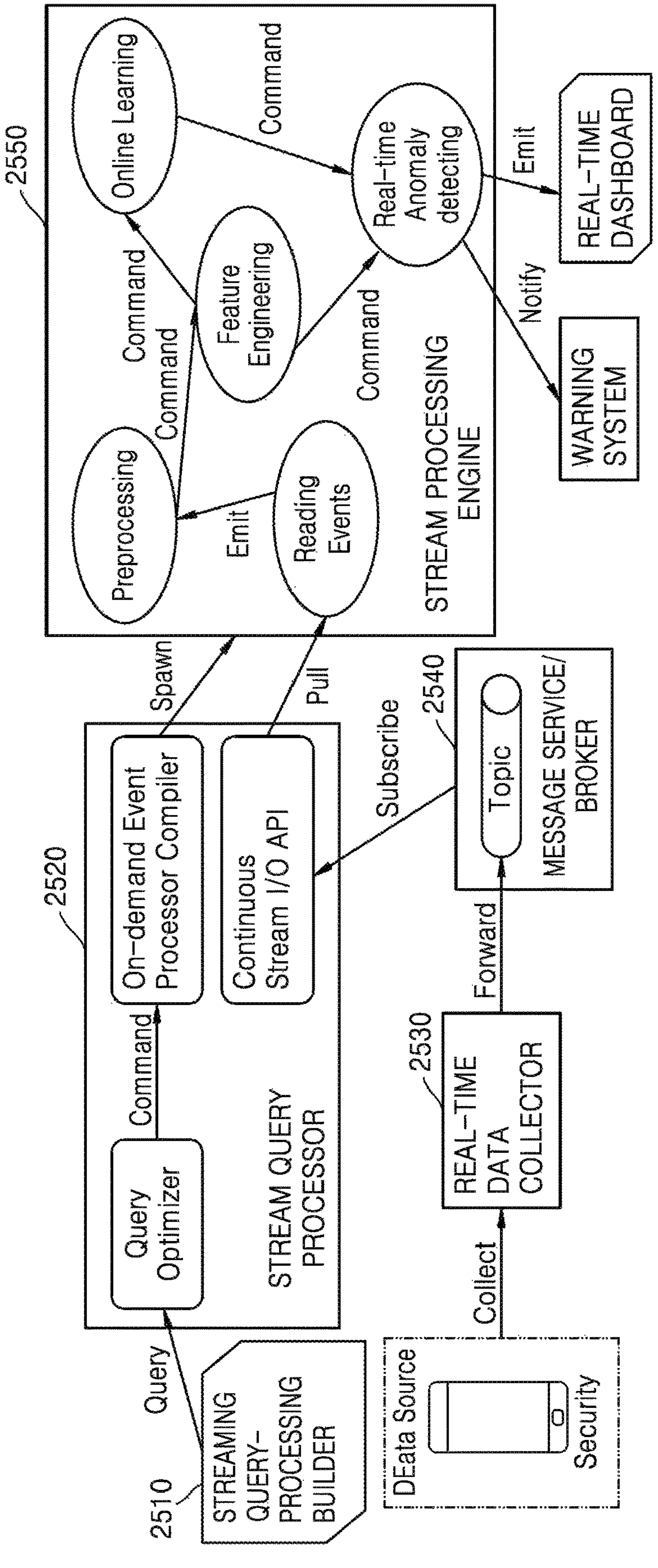
FIG. 25 shows a detailed overview of a system for detecting an anomaly and a data flow.

FIG. 25 shows a detailed overview of a system for detecting an anomaly and a data flow.

As shown in FIG. 25, a developer or a business analyst as a system administrator may build a streaming query-processing workflow using streaming query processing builder 2510. As described with reference to FIGS. 12 to 14, the streaming query-processing workflow may be built through, for example, a computer or a mobile device. After a user or the administrator completely configures each node through a streaming query-processing workflow designer and finalizes all settings, the workflow may be compiled and launched.

The workflow as a node graph may be converted into code up to a Java archive (JAR) file by a streaming query-processor 2520.

Next, the JAR file may be transferred to a stream-processing engine (SPE) 2550 for computation.

Streaming data is collected by a real-time data collector 2530 and distributed to topics of a message service/broker 2540. A continuous stream input/output (I/O) API in the streaming-query processor 2520 continuously processes read streaming data. Then, the SPE 2550 may receive input data for additional computation. The SPE 2550 may perform main computation for anomaly detection. There is a real-time dashboard for an analysis and response (warning) system in a subsequent computational loop process.

A method and system for detecting an anomalous event in REST API calls within connected applications/sensors according to example embodiments are provided. The method and system are designed to rapidly detect an anomaly and have high adaptability, and thus are useful for an early warning system.

An operating method of an apparatus for detecting an anomaly according to example embodiments may be implemented in the form of program instructions that may be executed through a variety of computing means and recorded in a computer-readable recording medium. The computer-readable recording medium may include program instructions, data files, data structures, and the like solely or in combination. The program instructions recorded in the computer-readable recording medium may be instructions specially designed and constructed for the present disclosure or instructions publicized to and used by those of ordinary skill in the computer software field. Examples of the computer-readable recording medium include magnetic media, such as a hard disk, a floppy disk, and a magnetic tape, optical media, such as a CD-ROM and a digital video disc (DVD), magneto-optical media, such as a floptical disk, and hardware devices specially constructed to store and execute program instructions, such as a ROM, a RAM, a flash memory, and the like. Examples of the program instructions include high-level language codes that can be executed by a computer using an interpreter or the like as well as machine language codes generated by a compiler.

It should be understood that example embodiments described herein should be considered in a descriptive sense only and not for purposes of limitation. Descriptions of features or aspects within each embodiment should typically be considered as available for other similar features or aspects in other example embodiments.

While one or more embodiments have been described with reference to the figures, it will be understood by those of ordinary skill in the art that various changes in form and details may be made therein without departing from the spirit and scope as defined by the following claims.

What is claimed is:

1. An apparatus for detecting an anomaly, the apparatus comprising:

a communication interface;

a memory including one or more instructions; and a processor configured to execute the one or more instructions to:

receive, through the communication interface, one or more application programming interface (API) calls corresponding to one or more applications from a terminal device, identify whether the anomaly has occurred in a first pattern of data acquired from the received API calls, by using a second pattern of data stored in a database, and based on identifying that the anomaly has occurred, transmit, through the communication interface, a notification indicating that the anomaly has occurred to the terminal device, wherein the first pattern of data comprises a first relative entropy matrix of API call data, and the second pattern of data comprises a second relative entropy matrix of API call data, and wherein the processor identifies whether the anomaly has occurred in the first pattern of data, based on a statistical comparison of the first relative entropy matrix and the second relative entropy matrix.

2. The apparatus of claim 1, wherein the processor is further configured to:

identify whether the first pattern of the data acquired from the received API calls deviates from the second pattern of the data stored in the database; and identify that the anomaly has occurred based on identifying that the first pattern of the data acquired from the received API calls deviates from the second pattern of the data stored in the database.

3. The apparatus of claim 1, wherein the processor is further configured to:

perform preprocessing;

extract a feature;

perform learning through a learning model; and make a prediction to determine whether the anomaly has occurred.

4. The apparatus of claim 1, wherein the processor is further configured to:

receive the one or more API calls generated by a transactional application from the terminal device; and identify whether the anomaly has occurred, by using the first pattern of the data acquired from the received API calls and a transactional data pattern stored in the database.

5. The apparatus of claim 4, wherein the transactional application is at least one of an e-commerce application, a bank transaction application, and a coupon reward application.

6. The apparatus of claim 1, wherein the processor is further configured to:

receive the one or more API calls generated by a sensing application from the terminal device; and identify whether the anomaly has occurred, by using the first pattern of the data acquired from the received API calls and a sensing data pattern stored in the database.

7. The apparatus of claim 6, wherein the sensing application is at least one of an Internet of things (IoT) application, a healthcare application, and a location information detection application.

8. The apparatus of claim 1, wherein, when the one or more applications are transactional applications, the data acquired from the API calls is the API calls; and wherein, when the one or more applications are sensing applications, the data acquired from the API calls is signal data transferred through the API calls.

9. An operating method of an apparatus for detecting an anomaly, the operating method comprising:

receiving, through a communication interface of the apparatus, one or more application programming interface (API) calls corresponding to one or more applications from a terminal device;

identifying whether the anomaly has occurred in a first pattern of data acquired from the received API calls, by using a second pattern of data stored in a database; and transmitting, through the communication interface, a notification indicating that the anomaly has occurred to the terminal device based on identifying that the anomaly has occurred, wherein the first pattern of data includes a first relative entropy matrix of API call data, and the second pattern of data includes a second relative entropy matrix of API call data, and wherein the identifying comprises identifying whether the anomaly has occurred in the first pattern of data, based on a statistical comparison of the first relative entropy matrix and the second relative entropy matrix.

10. The operating method of claim 9, wherein the identifying whether the anomaly has occurred comprises:

identifying whether the first pattern of the data acquired from the received API calls deviates from the second pattern of the data stored in the database; and identifying that the first pattern of the data acquired from the received API calls deviates from the second pattern of the data stored in the database, identifying that the anomaly has occurred.

11. The operating method of claim 9, wherein the identifying whether the anomaly has occurred comprises performing preprocessing, extracting a feature, performing learning through a learning model, and making a prediction to identify whether the anomaly has occurred.

12. The operating method of claim 9, wherein the notification is transmitted via at least one of e-mail and short message service (SMS).

13. The operating method of claim 9, wherein the one or more API calls are generated by a transactional application; and wherein the identifying of whether the anomaly has occurred comprises identifying whether the anomaly has occurred, by using the first pattern of the data acquired from the received API calls and a transactional data pattern stored in the database.

14. The operating method of claim 13, wherein the transactional application is at least one of an e-commerce application, a bank transaction application, and a coupon reward application.

15. The operating method of claim 9, wherein the one or more API calls are generated by a sensing application from the terminal device, and wherein the identifying whether the anomaly has occurred comprises identifying whether the anomaly has occurred, by using the first pattern of the data acquired from the received API calls and a sensing data pattern stored in the database.

16. The operating method of claim 15, wherein the sensing application is at least one of an Internet of things (IoT) application, a healthcare application, and a location information detection application.

17. The operating method of claim 9, wherein, when the one or more applications are transactional applications, the data acquired from the API calls is the API calls; and wherein, when the one or more applications are sensing applications, the data acquired from the API calls is signal data transferred through the API calls.

18. A non-transitory computer-readable recording medium having recorded thereon a program, which, when executed by a computer, performs operations for detecting an anomaly comprising:

receiving, through a communication interface of the computer, one or more application programming interface (API) calls corresponding to one or more applications from a terminal device;

identifying whether the anomaly has occurred in a first pattern of data acquired from the received API calls, by using a second pattern of data stored in a database; and transmitting, through the communication interface, a notification indicating that the anomaly has occurred to the terminal device based on identifying that the anomaly has occurred, wherein the first pattern of data includes a first relative entropy matrix of API call data, and the second pattern of data includes a second relative entropy matrix of API call data, and wherein the identifying comprises identifying whether the anomaly has occurred in the first pattern of data, based on a statistical comparison of the first relative entropy matrix and the second relative entropy matrix.

19. The apparatus of claim 1, wherein the processor is further configured to generate an anomaly detection report for a plurality of users indicating a probability of an activity of each user being anomalous.

* * * * *